US008088601B2

(12) United States Patent
Fox et al.

(10) Patent No.: US 8,088,601 B2
(45) Date of Patent: Jan. 3, 2012

(54) EXPRESSION SYSTEMS FOR FUNCTIONAL MEMBRANE POLYPEPTIDES

(75) Inventors: Brian G. Fox, Madison, WI (US); Pablo Sobrado, Blacksburg, VA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 325 days.

(21) Appl. No.: 12/267,825

(22) Filed: Nov. 10, 2008

(65) Prior Publication Data
US 2010/0330649 A1 Dec. 30, 2010

Related U.S. Application Data

(60) Provisional application No. 61/003,249, filed on Nov. 15, 2007.

(51) Int. Cl.
C12P 21/04 (2006.01)
C12P 15/09 (2006.01)
C12N 15/00 (2006.01)
C12N 9/48 (2006.01)
C07H 21/04 (2006.01)
C07K 17/00 (2006.01)

(52) U.S. Cl. ............. 435/69.7; 435/69.1; 435/68.1; 435/320.1; 435/212; 536/23.1; 536/23.2; 536/23.4; 530/324; 530/350

(58) Field of Classification Search ............. 435/69.7, 435/69.1, 68.1, 320.1, 212; 536/23.1, 23.2, 536/23.4; 530/324, 350
See application file for complete search history.

(56) References Cited

U.S. PATENT DOCUMENTS

| | | | |
|---|---|---|---|
| 5,132,213 | A | 7/1992 | Bachmair et al. |
| 5,270,176 | A | 12/1993 | Dorschug et al. |
| 5,643,758 | A | 7/1997 | Guan et al. |
| 5,831,018 | A | 11/1998 | Hillman et al. |
| 6,083,704 | A | 7/2000 | Hillman et al. |
| 2005/0227306 | A1* | 10/2005 | Fox et al. ............. 435/23 |

FOREIGN PATENT DOCUMENTS

JP 2005225796 * 8/2005

OTHER PUBLICATIONS

Abe et al., "Amino Acid Sequences of Cytochrome $b_5$ from Human, Porcine, and Bovine Erythrocytes and Comparison with Liver Microsomal Cytochrome $b_5$," *J. Biochem.*, 97(6):1659-1668 (1985).
Argos and Mathews, "The Structure of Ferrocytochrome $b_5$ at 2.8 Å Resolution," *J. Biol. Chem.*, 250(2):747-751 (1975).
Ausubel et al., "*Current Protocols in Molecular Biology*," vols. 1-4, John Wiley & Sons, Inc., New York, NY (1987-2004).
Blommel et al., "High Efficiency Single Step Production of Expression Plasmids from cDNA Clones Using the Flexi Vector Cloning System," *Protein Expr. Purif.*, 47:562-570 (2006).
Blommel et al., "Enhanced Bacterial Protein Expression During Auto-Induction Obtained by Alteration of Lac Repressor Dosage and Medium Composition," *Biotechnol. Prog.*, 23:585-598 (2007).
Blommel and Fox, "A Combined Approach to Improving Large-Scale Production of Tobacco Etch Virus Protease," *Protein Expr. Purif.*, 55:53-68 (2007).
Boos and Shuman, "Maltose/Maltodextrin System of *Escherichia coli*: Transport, Metabolism, and Regulation," *Microbiol. Molec. Biol. Rev.* 62(1): 204-229 (1998).
Bradford, "A Rapid and Sensitive Method for the Quantitation of Microgram Quantities of Protein Utilizing the Principle of Protein-Dye Binding," *Anal. Biochem.*, 72:248-252 (1976).
Brambillasca et al., "Unassisted Translocation of Large Polypeptide Domains Across Phospholipid Bilayers," *J. Cell Biology*, 175(5):767-777 (2006).
Burgess et al., "Poly(ethylene Glycol)-Induced Lipid Mixing But Not Fusion between Synthetic Phosphatidylcholine Large Unilamellar Vesicles," *Biochemistry*, 30:4193-4200 (1991).
Crooke and Wickner, "Trigger Factor: A Soluble Protein that Folds Pro-OmpA Into a Membrane-Assembly-Competent Form," *Proc. Natl. Acad. Sci. USA*, 84:5216-5220 (1987).
Dieffenbach et al., *PCR Primer: A Laboratory Manual*, Cold Spring Harbor Laboratory Press, Cold Spring Harbor, NY (1995).
Enoch et al., "Mechanism of Rat Liver Microsomal Stearyl-CoA Desaturase," *J. Biol. Chem.*,. 251(16):5095-5103 (1976).
Enoch et al., "Cytochrome $b_5$ and Cytochrome $b_5$ Reductase-Phospholipid Vesicles," *J. Biol. Chem.*, 252(16):5656-5660 (1977).
Estabrook and Werringloer, "The Measurement of Difference Spectra: Application to the Cytochromes of Microsomes," *Microsomal Electron Transport and Cyt P-450*, 22:212-220 (1978).
Hegesh et al., "Congenital Methemoglobinemia with a Deficiency of Cytochrome $b_5$," *N. Engl. J. Med.*, 314(12):757-761 (1986).
Hessa et al., "Recognition of Transmembrane Helices by the Endoplasmic Reticulum Translocon," *Nature*, 433:377-381 (2005).
Hoffman et al., "Lactose Fed-Batch Overexpression of Recombinant Metalloproteins in *Escherichia coli* BL21 (DE3): Process Control Yielding High Levels of Metal-Incorporated, Soluble Protein," *Protein Expr. Purif.*, 6:646-654 (1995).
Holmgren, "Thioredoxin and Glutaredoxin Systems," *J. Biol. Chem.*, 264(24):13963-13966 (1989). Kapust and Waugh, "*Escherichia coli* Maltose-Binding Protein is Uncommonly Effective at Promoting the Solubility of Polypeptides to Which it is Fused," *Protein Sci.*, 8:1668-1674 (1999).
Kriegler, *Gene Transfer and Expression: A Laboratory Manual*, Stockton Press, New York, NY (1990).
Kroliczewski et al., "In vitro Reconstitution of the Spinach Chloroplast Cytochrome $b_6$ Protein from a Fusion Protein Expressed in *Escherichia coli*," Biochim. Biophys. Acta, 1598:177-184 (2002).
Lederer, "The Cytochrome $b_5$-fold: An Adaptable Module," *Biochimie*, 76:674-692 (1994).
Lloyd et al., "Recombinant Human Erythrocyte Cytochrome $b_5$," *Biochemistry*, 33:11432-11437 (1994).
Ludlam et al., "The Crystal Structure of Ribosomal Chaperone Trigger Factor from *Vibrio cholerae*," *Proc. Natl. Acad. Sci. USA*, 101(37):13436-13441 (2004).

(Continued)

Primary Examiner — Ganapathirama Raghu
(74) *Attorney, Agent, or Firm* — Quarles & Brady, LLP

(57) ABSTRACT

Expression systems and methods for the expression of functional membrane polypeptides such as human cytochrome b5 are provided. The systems include recombinant expression vectors capable of expressing soluble fusion proteins that include a solubilizing agent, a linker, and a membrane polypeptide, as well as one or more cleavers, e.g. proteases, capable of cleaving the linker to release the membrane polypeptide. When the fusion protein is expressed, the linker is cleaved by the cleaver to allow association of the membrane polypeptide with a membrane.

22 Claims, 7 Drawing Sheets

OTHER PUBLICATIONS

Mihara and Sato, "Partial Purification of NADH-Cytochrome $b_5$ Reductase from Rabbit Liver Microsomes with Detergents and its Properties," *J. Biochem.*, 71(4):725-735 (1972).

Miyaji et al., "Expression of Human Lymphotoxin Derivatives in *Escherichia coli* and Comparison of Their Biological Activity in Vitro," *Agric. Biol. Chem.*, 53(1):277-279 (1989).

Mulrooney and Waskell, "High-Level Expression in *Escherichia coli* and Purification of the Membrane-Bound Form of Cytochrome $b_5$," *Protein Expr. Purif.*, 19:173-178 (2000).

Nguyen et al., "An Automated Small-Scale Protein Expression and Purification Screening Provides Beneficial Information for Protein Production," *J. Struct. Funct. Genomics*, 5:23-27 (2004).

Nomura et al., "Direct Preparation of Giant Proteo-Liposomes by in vitro Membrane Protein Synthesis," *J. Biotechnol.*, 133:190-195 (2008).

Nygren et al., "Engineering Proteins to Facilitate Bioprocessing," *Trends Biotechnol.*, 12:184-188 (1994).

Ogishima et al., "Identification of Outer Mitochondrial Membrane Cytochrome $b_5$ as a Modulator for Androgen Synthesis in Leydig Cells," *J. Biol. Chem.*, 278(23):21204-21211 (2003).

Popot and Engelman, "Helical Membrane Protein Folding, Stability, and Evolution," *Annu. Rev. Biochem.*, 69:881-922 (2000).

Porter, "The Roles of Cytochrome $b_5$ in Cytochrome P450 Reactions," *J. Biochem. Mol. Toxicol.*, 16(6):311-316 (2002).

Power et al., "High, Level Expression of a Truncated Chicken Progresterone Receptor in *Escherichia coli*," *J. Biol. Chem.*, 265(3):1419-1424 (1990).

Pryor and Leiting, "High-Level Expression of Soluble Protein in *Escherichia coli* Using a His$_6$-Tag and Maltose-Binding-Protein Double-Affinity Fusion System," *Protein Exp. Purif.* 10:309-319 (1997).

Sambrook et al., *Molecular Cloning: A Laboratory Manual*, third edition, Cold Spring Harbor Laboratory Press, Cold Spring Harbor, NY (2000).

Samuelsson et al., "Enhanced in vitro Refolding of Insulin-Like Growth Factor I Using a Solubilizing Fusion Partner," *Biochemistry*, 33:4207-4211 (1994).

Schenkman and Jansson, "The Many Roles of Cytochrome $b_5$," *Pharmacol. Ther.*, 97:139-152 (2003).

Sekine et al., "Cloning and Expression of cDNA for Salmon Growth Hormone in *Escherichia coli*," *Proc. Natl. Acad. Sci. USA.*, 82:4306-4310 (1985).

Sobrado et al., "A Protein Structure Initiative Approach to Expression, Purification, and in Situ Delivery of Human Cytochrome b5 to Membrane Vesicles," *Protein Expr. Purif.*, 58:229-241 (2008).

Spatz and Strittmatter, "A Form of Cytochrome $b_5$ That Contains an Additional Hydrophobic Sequence of 40 Amino Acid Residues," *Proc. Natl. Acad. Sci. USA*, 68(5):1042-1046 (1971).

Sperling et al., "A Cytochrome-$b_5$-Containing Fusion Protein Similar to Plant Acyl Lipid Desaturases," *Eur. J. Biochem.*, 232:798-805 (1995).

Sreenath et al., "Protocols for Production of Selenomethionine-Labeled Proteins in 2-L Polyethylene Terephthalate Bottles Using Auto-Induction Medium," *Protein Expr. Purif.*, 40:256-267 (2005).

Stevens, "Design of High-Throughput Methods of Protein Production for Structural Biology," *Structure*, 8:R177-R185 (2000).

Strausberg et al., "The Mammalian Gene Collection," *Science*, 286:455-457 (1999).

Strittmatter et al., "Incorporation of Microsomal Electron-Transfer Components into Liposomes: Considerations for Diffusion-Limited Reactions," *Methods Enzymol.*, 52:206-211 (1978).

Tamm, ed., *Protein-Lipid Interactions*, Wiley-VCH, Weinheim, Germany (2005).

Vergeres and Waskell, "Cytochrome b$_5$, its Functions, Structure and Membrane Topology," *Biochimie*, 77:604-620 (1995).

Vinarov et al., "Wheat Germ Cell-Free Platform for Eukaryotic Protein Production," *FEBS J.*, 273:4160-4169 (2006).

von Bodman, et al., "Synthesis, Bacterial Expression, and Mutagenesis of the Gene Coding for Mammalian Cytochrome $b_5$," *Proc. Natl. Acad. Sci. USA*, 83:9443-9447 (1986).

Yabal et al., "Translocation of the C Terminus of a Tail-Anchored Protein Across the Endoplasmic Reticulum Membrane in Yeast Mutants Defective in Signal Peptide-Drive Translocation," *J. Biol. Chem.*, 278(5):3489-3496 (2003).

Yao et al., "X-Ray Crystallography, CD and Kinetic Studies Revealed the Essence of the Abnormal Behaviors of the Cytochrome $b_5$ Phe35→Tyr Mutant," *Eur. J. Biochem.*, 269:4287-4296 (2002).

Yanisch-Perron et al., "Improved M13 Phage Cloning Vectors and Host Strains: Nucleotide Sequences of the M13mp18 and pUC19 Vectors," *Gene*, 33:103-119 (1985).

Zhang et al., "Expression of Eukaryotic Proteins in Soluble Form in *Escherichia coli*," *Protein Exp. Purif.*, 12:159-165 (1998).

Begum et al., "Purification of the Membrane Binding Domain of Cytochrome $b_5$ by Immobilised Nickel Chelate Chromatography," *J. of Chromatography B*, 737:119-130 (2000).

Lin et al., "Expression of Lipase-Solubilized Bovine Liver Microsomal Cytochrome $b_5$ in *Escherichia coli* as a Glutathione S-transferase Fusion Protein (GST-cyt $b_5$)," *Protein Expression and Purification*, 45:352-358 (2006).

Sachdev and Chrigwin, "Solubility of Proteins Isolated from Inclusion Bodies is Enhanced by Fusion to Maltose-Binding Protein or Thioredoxin," *Protein Expression and Purification*, 12(1):122-132 (1998).

Smith et al., "Tobacco Cytochrome $b_5$: cDNA Isolation, Expression Analysis and in vitro Protein Targeting," *Plant Molecular Biology*, 25:527-537 (1994).

International Search Report dated Mar. 30, 2009 for related PCT Application No. PCT/US2008/083503.

* cited by examiner

FIGURE 1

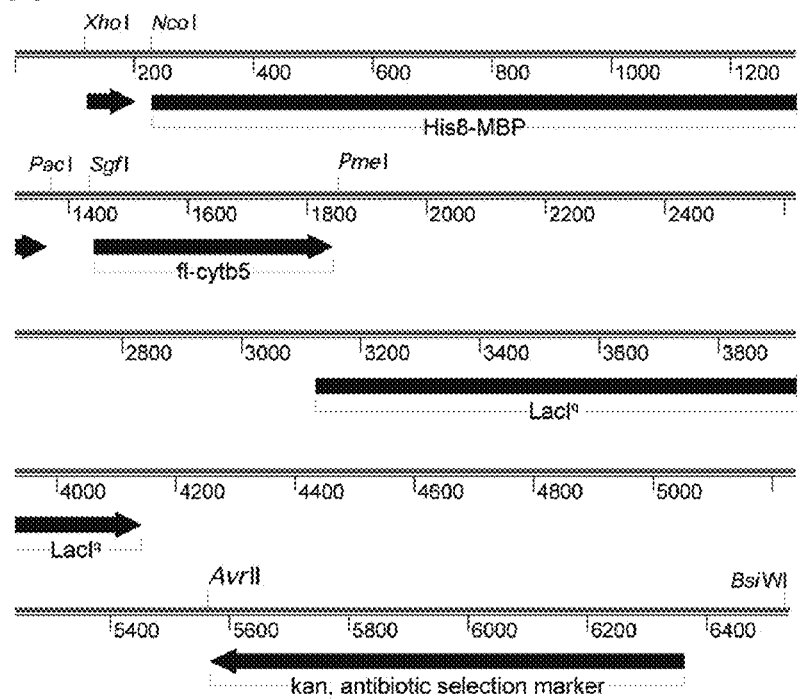

B

MGHHHHHHHHASKIEEGKLVIWINGDKGYNGLAEVGKKFE 40
KDTGIKVTVEHPDKLEEKFPQVAATGDGPDIIFWAHDRFG 80
GYAQSGLLAEITPDKAFQDKLYPFTWDAVRYNGKLIAYPI 120
AVEALSLIYNKDLLPNPPKTWEEIPALDKELKAKGKSALM 160
FNLQEPYFTWPLIAADGGYAFKYENGKYDIKDVGVDNAGA 200
KAGLTFLVDLIKNKHMNADTDYSIAEAAFNKGETAMTING 240
PWAWSNIDTSKVNYGVTVLPTFKGQPSKPFVGVLSAGINA 280
ASPNKELAKEFLENYLLTDEGLEAVNKDKPLGAVALKSYE 320
EELAKDPRIAATMENAQKGEIMPNIPQMSAFWYAVRTAVI 360
NAASGRQTVDEALKDAQTLINGDGAGLEVLFQGP*ENLYFQ* 400
AIAEMAEQSDEAVKYYTLEEIQKHNHSKSTWLILHHKVYD 440
LTKFLEEHPGGEEVLREQAGGDATENFEDVGHSTDAREMS 480
KTFIIGELHPDDRPKLNKPPETLITTIDSSSSWWTNWVIP 520
AISAVAVALMYRLYMAED 538

C

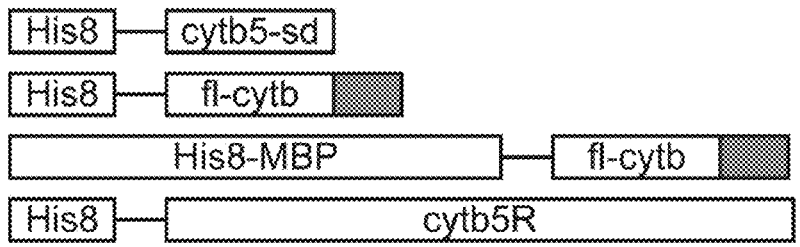

FIGURE 2
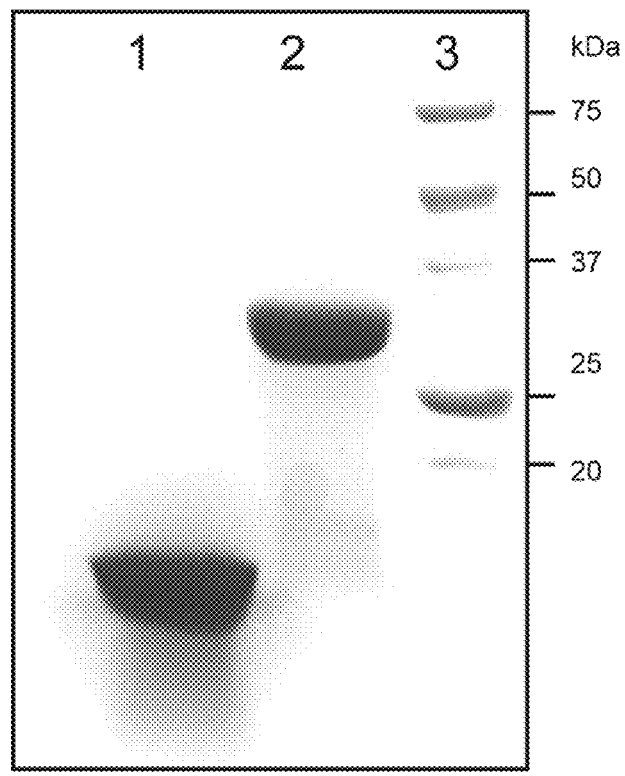
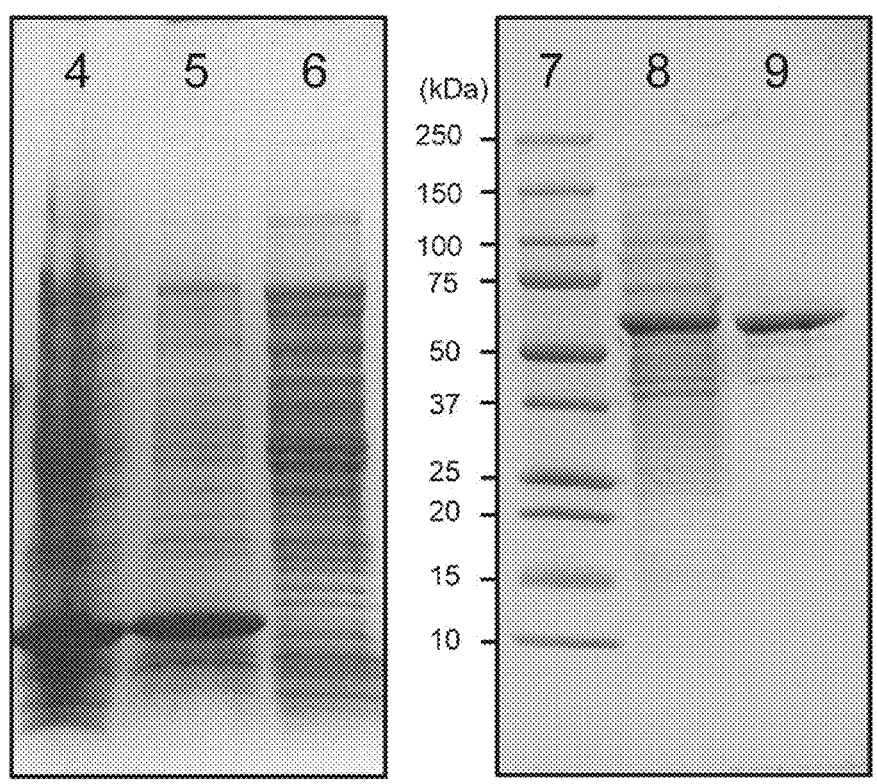

EXPRESSION SYSTEMS FOR FUNCTIONAL MEMBRANE POLYPEPTIDES

CROSS-REFERENCE TO RELATED APPLICATIONS

This invention claims priority to U.S. Provisional Patent Application Ser. No. 61/003,249, filed Nov. 15, 2007, which is herein incorporated by reference.

GOVERNMENT INTERESTS

This invention was made with United States government support awarded by the following agency: National Institutes of Health (NIH) grant No. GM50853. The United States government has certain rights in this invention.

FIELD OF THE INVENTION

This invention is related to the biochemical arts. The present invention provides an expression system for functional membrane polypeptides such as human cytochrome b5.

BACKGROUND OF THE INVENTION

Although it is usually possible to achieve a favorable yield of a recombinant protein in *Escherichia coli*, using this method to obtain a recombinant protein in a functional form continues to be a major challenge. Sometimes this problem can be overcome by fusing an aggregation-prone polypeptide to a highly soluble partner. However, even the fusion of a highly soluble partner to a desired target protein often results in the expression of a protein that rapidly precipitates out of solution, a recombinant protein that is non-functional or poorly functional, and/or a protein that is biologically inactive. Direct constitution of membrane proteins into giant liposomes in cell-free (in vitro) protein synthesis was recently investigated by Nomura et al., 2007, *J. Biotechnol.* 2007 Aug. 17; [Epub ahead of print]. However, these authors described the expression of apo-cytb5 and have not addressed how to get the heme into the protein.

The cytochromes are a group of chromophoric proteins that serve as electron carriers in the electron transport processes of cells. They convert the high-energy electrons derived from the metabolism of carbohydrates, fats, and other foodstuffs into ATP, the primary source of energy for cells. Cytochromes are related to one another by the presence of a bound heme group consisting of a porphyrin ring containing a tightly bound iron atom, which serves as an electron carrier by changing from the ferric to the ferrous state when accepting an electron. Cytochromes accept electrons from substrates such as NADH or $FADH_2$ and pass them on to other electron carriers such as other cytochromes or ubiquinone. Cytochromes b (cyt b) are electron transfer proteins having one or two haem b groups noncovalently bound to the protein. Cytochromes b possess a wide range of properties and function in a large number of different redox processes (reviewed in Kiel, 1995, *Type-b Cytochromes: Sensors and Switches*, CRC Press, Boca Raton, Fla.).

Cytochrome b5 (also "cytb5" or "$cytb_5$") is present in bacteria, protozoans, yeasts, and mammals (Lederer, 1994, *Biochimie* 76: 674-692). The protein consists of an N-terminal hydrophilic heme-binding domain of approximately 100 residues, and a C-terminal hydrophobic membrane anchor domain of approximately 30 residues (Argos and Mathews, 1975, *J. Biol. Chem.* 250: 747-751; Vergeres and Waskell, 1995, *Biochimie* 77: 604-620). The amino acid sequences of cytochrome $b_5$ from human, porcine, and bovine erythrocytes have been identified (Abe et al., 1985, *J. Biochem.* 97: 1659-1668). In mammals, isoforms of cytb5 are present in the endoplasmic reticulum, mitochondria, and erythrocytes. The endoplasmic and mitochondrial $cytb_5$ are expressed from different genes, while the erythrocyte isoform is thought to originate from post-translational proteolysis of the endoplasmic protein. Since erythrocyte cytb5 lacks the C-terminal membrane anchor domain, it functions as a soluble protein in blood cells (Lloyd et al., 1994, *Biochemistry* 33: 11432-11437). Erythrocyte cytb5 is responsible for the reduction of non-functional ferric met-hemoglobin to the $O_2$-binding ferrous form.

In the endoplasmic reticulum, cytb5 is attached to the cellular membrane through the C-terminal membrane anchor domain, where it participates in the electron transfer steps of many essential physiological reactions including fatty acid desaturation, biosynthesis of plasmalogen and cholesterol, and reduction of cytochrome P450 (Vergeres and Waskell, 1995, *Biochimie* 77: 604-620). Membrane-bound mitochondrial cytb5 is involved in androgenesis in rat Leydig cells. Initial structural and functional studies of cytb5 were performed on samples purified from rabbit, rat, and cow liver, due to the high concentration of cytb5 present in these tissues. Biochemical and biophysical characterization of the detergent solubilized full-length microsomal cytb5, and the heme-binding domain liberated by proteolysis, have also been provided (Strittmatter et al., 1978, *Methods Enzymol.* 52: 206-211). Notably, full-length cytb5 (fl-cytb5) spontaneously associates with synthetic lipids, and fl-cytb5 is required for stearoyl-CoA desaturase activity (Enoch et al., 1976, *J. Biol. Chem.* 251: 5095-5103; Enoch et al., 1977, *J. Biol. Chem.* 252: 5656-5660).

More recently, recombinant forms truncated to only the heme-binding cytb5 soluble domain (cytb5-sd) were also used for biochemical analysis and structural determinations (Yao et al., 2002, *Eur. J. Biochem.* 269: 4287-4296). Approaches for detergent solubilization of the full-length cytb5 protein from inclusion bodies, refolding, and incorporation of heme into the solubilized and refolded protein have also been developed. Cytochrome b5 containing fusion proteins have also been expressed (Sperling et al., 1995, *Eur. J. Biochem.* 232: 798-805). The codon-optimized rat cytb5-sd and the tobacco cytb5 have been expressed in *E. coli*. Approaches for detergent-mediated isolation of the full-length cytb5 (fl-cytb5) from membranes, incorporation of heme into the solubilized rabbit protein, preparation of the bovine protein as a fusion to glutathione-S-transferase and recovery of the fusion protein from membranes by lipase treatment, and purification of the expressed mouse protein from *E. coli* membranes have also been developed. These latter preparation approaches are labor intensive and time consuming.

Synthesizing large quantities of functional membrane polypeptides, including functional cytochrome b5, remains a challenge. It would be advantageous to provide compositions and methods for the expression of functional membrane polypeptides. The present invention addresses these and other related needs.

BRIEF SUMMARY OF THE INVENTION

Provided are systems for expressing membrane polypeptides. The systems include: a) recombinant expression vectors capable of expressing fusion proteins that comprise (1) a solubilizing agent, (2) a linker, and (3) a membrane polypeptide that includes a membrane anchor comprising an amino acid sequence at least 90% identical to the amino acid sequence of SEQ ID NO:7 or an amino acid sequence of SEQ ID NO:7 having 1 to 4 conservative amino acid substitutions; and b) a cleaver capable of cleaving the linker to release the membrane polypeptide. When the fusion protein is expressed, the linker can be cleaved by the cleaver to allow association of the membrane polypeptides with membranes. The fusion proteins may be soluble fusion proteins. The solubilizing agents may be maltose binding proteins. The fusion proteins may include a membrane anchor that includes an amino acid sequence at least 90% identical to the amino acid sequence of SEQ ID NO:6 or an amino acid sequence of SEQ ID NO:6 having 1 to 2 conservative amino acid substitutions. The fusion proteins may include proteases capable of cleaving the linkers. The fusion proteins may also include one or more affinity purification tags. The membrane polypeptide may be cytochrome b5, and in particular the membrane polypeptide may be human cytochrome b5.

In the systems of the present invention, the cleavers may be chemical agents. Alternatively, the cleavers may be enzymatic, e.g. the cleavers may be proteases. In particular, the cleavers may include or more of: tobacco etch virus (TEV) protease, a human rhinovirus 3C protease, or a tobacco vein mottling virus (TVMV) protease. In the systems of the present invention, the linkers are preferably about 4 to about 60 amino acid residues long. In the systems of the present invention, the membrane may be in the form of one or more of a lipid vesicle, a liposome, or a microsome.

Provided are methods for in vitro association of membrane polypeptides with membranes. The methods include: a) expressing fusion proteins comprising (1) a solubilizing agent, (2) a linker, and (3) a membrane polypeptide with a membrane anchor having an amino acid sequence at least 90% identical to the amino acid sequence of SEQ ID NO:7 or an amino acid sequence of SEQ ID NO:7 having 1 to 4 conservative amino acid substitutions; and b) providing a cleaver capable of cleaving the linker to release the membrane polypeptide. When the linker is cleaved by the cleaver, the membrane polypeptide can associate with the membrane. The fusion proteins may be soluble fusion proteins. The solubilizing agents may be maltose binding proteins. The fusion proteins may include a membrane anchor that includes an amino acid sequence at least 90% identical to the amino acid sequence of SEQ ID NO:6 or an amino acid sequence of SEQ ID NO:6 having 1 to 2 conservative amino acid substitutions. The fusion proteins may include proteases capable of cleaving the linkers. The fusion proteins may also include one or more affinity purification tags. The membrane polypeptide may be cytochrome b5, and in particular the membrane polypeptide may be human cytochrome b5.

In the practice of the methods of the present invention, the cleavers may be chemical agents. Alternatively, the cleavers may be enzymatic, e.g. the cleavers may be proteases. In particular, the cleavers may include or more of: tobacco etch virus (TEV) protease, a human rhinovirus 3C protease, or a tobacco vein mottling virus (TVMV) protease. In the methods of the present invention, the membrane may be in the form of one or more of a lipid vesicle, a liposome, or a microsome. In the practice of the methods, the linker may be cleaved immediately after expression of the fusion protein. Alternatively, the linker may be cleaved at any convenient or reasonable time after the expression of the fusion protein needed to advance subsequent uses.

BRIEF DESCRIPTION OF THE DRAWINGS

FIG. 1 (A) schematically illustrates pVP56K-fl-cytb5, an expression vector that can be used to practice the present invention, (B) shows the amino acid sequence of the His8-MBP-fl-cytb5 fusion protein (SEQ ID NO:8), and (C) schematically illustrates fusion proteins made according to the present invention.

FIG. 2 depicts images of Coomassie-stained SDS-PAGE gels showing expression and purification of full-length forms of cytb5.

DETAILED DESCRIPTION OF THE INVENTION

Figure 3:
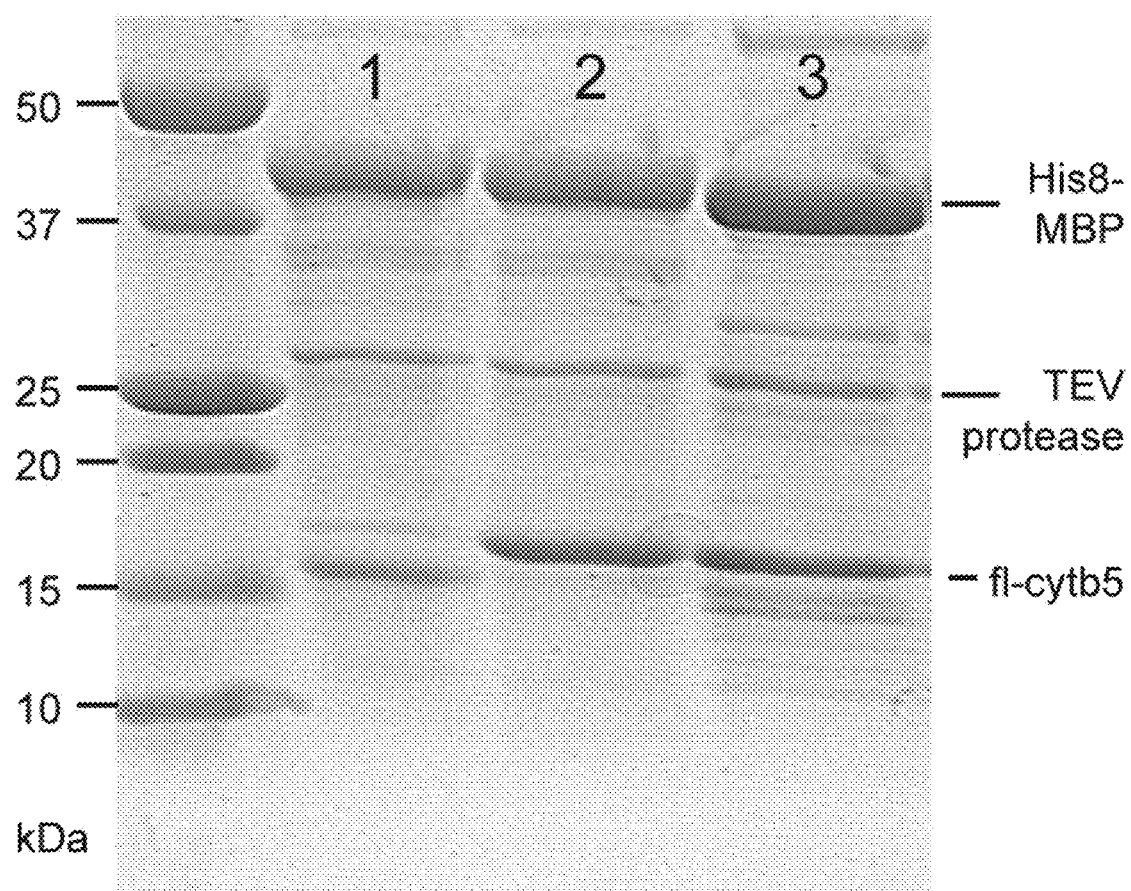
FIG. 3 depicts an image of a Coomassie-stained SDS-PAGE gel showing differences in post-translational processing caused by long-term auto-induction or short-term IPTG induction.

The present invention is made possible by the inventors' discovery that the carboxy terminus portion of the cytochrome b polypeptide functions as a membrane anchor. This sequence, while known (Abe et al., 1985, *J. Biochem.* 97: 1659-1668), had not previously been identified as having any particular function. By fusing this section onto other proteins, one can localize them into the membrane. Further, by further fusing a cleavable solubilizing sequence to the protein (or a solubilizing sequence fused to the protein via a cleavable linker), one can design systems that can be used to express the membrane bound protein in solution, optionally purify it, and then cleave the solubilizing agent so as to allow the protein to associate a with membrane.

It is contemplated that the methods of the present invention can be used with a variety of proteins, such as monotopic (or peripheral) membrane proteins, including but not limited to full-length cytb5R, peptidoglycan glycosyltransferases (N-terminal membrane anchors), prostaglandin H2 synthase-1 (internal sequences and secondary structures serving as membrane anchors), monoamine oxidase B, cyclooxygenase-2, carnitine palmitoyl transferase, and many others. For those proteins that have a C-terminal membrane anchor, the present invention provides for the potential use of His8-MBP as a carrier for the full length, otherwise insoluble protein, and the potential for in situ transfer into a biological membrane environment for expression of functional membrane polypeptides. For those proteins that do not have a C-terminal membrane anchor, the present invention provides for the addition of such a membrane anchor that can provide the function of association of the protein with membranes, thus ensuring functionality of the particular membrane protein. For those proteins that have an N-terminal membrane anchor, it is also possible to replace the N-terminal membrane anchor with a C-terminal membrane anchor according to the present invention, or to add a C-terminal membrane anchor in addition to the already present N-terminal membrane anchor.

It is also contemplated that the methods of the present invention can be practiced with a variety of human and non-human cytochromes. Examples of other cytochromes suitably include the family of b5-like cytochromes, including but not limited to, cytochrome b5 itself, cytochromes with hemoprotein domains covalently associated with other redox proteins, such as in flavocytochrome b2 (L-lactate dehydrogenase), sulfite oxidase, and assimilatory nitrate reductase (Lederer, 1994, *Biochimie* 76: 674-692), plant and fungal nitrate reductases, and plant and fungal cytochrome b5/acyl lipid desaturase fusion proteins. In one preferred example, the methods of the present invention are practiced with human cytochrome b5.

"Solubility" refers to the degree to which a substance dissolves in a solvent to make a solution. For example, globular proteins are soluble and many of these are enzymes. "Solubilizing agent" is an agent that makes a substance more soluble, especially in an aqueous solution. For example, maltose binding protein acts as a solubilizing agent when it is co-expressed with a target protein, thereby making the expressed target protein more soluble in an aqueous solution. Suitable solubilizing agents include, but are not limited to, maltose binding protein, thioredoxin, glutathione S-transferase, NusA, lysozyme, glycerol, ethylene glycol, arginine, betaine, and many other substances known to those skilled in the art.

The practice of the present invention employs, unless otherwise indicated, conventional techniques of molecular biology (including recombinant techniques), microbiology, cell biology, biochemistry, immunology, protein kinetics, and mass spectroscopy, which are within the skill of art. Such techniques are explained fully in the literature, such as in Sambrook et al., 2000, *Molecular Cloning: A Laboratory Manual*, third edition, Cold Spring Harbor Laboratory Press, Cold Spring Harbor, N.Y.; Ausubel et al., 1987-2004, *Current Protocols in Molecular Biology*, Volumes 1-4, John Wiley & Sons, Inc., New York, N.Y.; Kriegler, 1990, *Gene Transfer and Expression: A Laboratory Manual*, Stockton Press, New York, N.Y.; Dieffenbach et al., 1995, *PCR Primer: A Laboratory Manual*, Cold Spring Harbor Laboratory Press, Cold Spring Harbor, N.Y., each of which is incorporated herein by reference in its entirety. Procedures employing commercially available assay kits and reagents typically are used according to manufacturer-defined protocols unless otherwise noted.

Generally, the nomenclature and the laboratory procedures in recombinant DNA technology described below are those well known and commonly employed in the art. Standard techniques are used for cloning, DNA, RNA, and protein isolation, nucleic acid amplification, and nucleic acid and protein purification. Generally enzymatic reactions involving DNA ligase, DNA polymerase, restriction endonucleases and the like are performed according to the manufacturer's specifications.

"Nucleic acid" or "polynucleotide sequence" refers to a single or double-stranded polymer of deoxyribonucleotide or ribonucleotide bases read from the 5' to the 3' end. Nucleic acids may also include modified nucleotides that permit correct read-through by a polymerase and do not alter expression of a polypeptide encoded by that nucleic acid.

"Nucleic acid sequence encoding" refers to a nucleic acid that directs the expression of a specific protein or peptide. The nucleic acid sequences include both the DNA strand sequence that is transcribed into RNA, and the RNA sequence that is translated into protein. The nucleic acid sequences include both the full length nucleic acid sequences as well as non-full length sequences derived from the full length sequences. It should be further understood that the sequence includes the degenerate codons of the native sequence or sequences that may be introduced to provide codon preference in a specific host cell.

"Coding sequence" or "coding region" refers to a nucleic acid molecule having sequence information necessary to produce a gene product, when the sequence is expressed.

"Nucleic acid construct" or "DNA construct" refers to a coding sequence or sequences operably linked to appropriate regulatory sequences so as to enable expression of the coding sequence.

"Isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated nucleic acid of the present invention is separated from open reading frames that flank the desired gene and encode proteins other than the desired protein. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 25% sequence identity. Alternatively, percent identity can be any integer from 25% to 100%. More preferred embodiments include at least: 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98% or 99% compared to a reference sequence using the programs described herein; preferably BLAST using standard parameters, as described. One of skill will recognize that these values can be appropriately adjusted to determine corresponding identity of proteins encoded by two nucleotide sequences by taking into account codon degeneracy, amino acid similarity, reading frame positioning and the like.

"Substantial identity" of amino acid sequences for purposes of this invention normally means polypeptide sequence identity of at least 40%. Preferred percent identity of polypeptides can be any integer from 40% to 100%. More preferred embodiments include at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99%. Polypeptides that are "substantially identical" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

A protein "isoform" is a version of a protein with some small differences. For example, the small differences may be a result of a splice variant of the protein, or they may be the result of some post-translational modification. Often, an isoform of an enzyme may have different catalytic properties than the native form of the enzyme.

"Fusion protein" refers to a protein created through genetic engineering from two or more proteins or polypeptides. This is achieved by creating a fusion gene: removing the stop codon from the DNA sequence of the first protein, then appending the DNA sequence of the second protein in frame. That DNA sequence will then be expressed by a cell as a single protein. An example of a fusion protein is a fusion protein that includes: (i) a maltose binding protein as a first protein, (ii) optionally a linker, and (iii) a human cytochrome b5. Expression of this fusion protein results in expression of maltose binding protein, linker, and human cytochrome b5.

Often "linker" (or "spacer") domain or peptide is also added between the first and the second protein or polypeptide. The linker typically makes it more likely that the expressed proteins fold independently and have biological activity or functionality. Especially in the case where the linkers enable protein purification, linkers in protein fusions are sometimes engineered with cleavage sites for proteases or chemical agents which enable the liberation of the two separate proteins.

In some embodiments, the present invention contemplates the use of a linker (i.e. linker domain that comprises amino acid residues). The length of the linker may vary. In some embodiments, the length of the linker is about 4 to about 60 amino acid residues, preferably it is about 5 to about 20 amino acid residues, and more preferably it is about 16 to about 34 amino acid residues. Once the fusion protein is expressed, in order to obtain the desired polypeptide, it has to be separated out of the fusion protein by cleavage, using a "cleaver". Cleavage of the linker can be accomplished in a variety of ways known in the art, using, for example, physical, and more preferably, chemical or enzymatic methods. Thus, the cleavers may include chemical agents, enzymes, or combinations thereof. Chemical methods are preferably used for cleavage, because it is relatively straightforward to make them appropriate for the sparingly soluble nature of the fusion protein. Methods for the selective cleavage of fusion proteins with a chemical agent are disclosed in U.S. Pat. No. 5,270,176, which is incorporated herein by reference. Enzymatic methods can also be used for cleavage of the linker. For example, a variety of proteases can be used as cleavers, for enzymatic cleavage of the linker. Generally, better protease specificity is achieved as the length of the linker is increased.

"Cytochromes b5" refer to ubiquitous electron transport hemoproteins found in animals, plants, fungi and purple phototrophic bacteria. Some of these are shown in Table 1. For a recent review on the many roles of cytochrome b5, see Schenkman and Jansson, 2003, *Pharmacol. Ther.* 97: 139-152. Synonymously with "cytb5" or "cytb$_5$", "fl-cytb5" is sometimes used here referring to "full-length cytochrome b5", to emphasize the full length of the cloned cytochrome b5 (as opposed to cytochrome b5 truncated to only the soluble domain, referred to as "cytb5-sd").

TABLE 1

| Localization and physiological roles of cytochrome b5 | | | |
| --- | --- | --- | --- |
| Localization | Active form | Function | Reference |
| Mitochondrion | Membrane bound | Androgenesis | Ogishima et al., 2003, J. Biol. Chem. 278: 21204-21211. |
| Endoplasmic reticulum | Membrane bound | Biosynthesis of unsaturated fatty acids (Δ5, Δ6, Δ9, Δ12); plasmalogens; cholesterol | Vergeres and Waskell, 1995, Biochimie 77: 604-620 |
| Endoplasmic reticulum | Membrane bound | Reduction of cytochrome P450s | Porter, 2002, J. Biochem. Mol. Toxicol. 16: 311-316 |
| Erythrocytes | Soluble | Reduction of hemoglobin | Hegesh et al., 1986, N. Engl. J. Med. 314: 757-761 |

In one aspect, the present invention contemplates the development of compounds such as a novel class of chemotherapeutics that can be anchored to membranes. "C-terminus" (also known as the "carboxyl-terminus", "carboxy-terminus", "C-terminal end", or "COOH-terminus") of a protein or polypeptide is the end of the amino acid chain terminated by a free carboxyl group (—COOH). For purposes of the present invention, C-terminus refers to the approximately 37 amino acids of the C-terminus of human cytochrome b5, TLITTIDSSSSWWTNWVIPAISAVAVALMYRLYMAED (shown as SEQ ID NO:7). Preferably, C-terminus refers to the approximately 19 amino acids of the C-terminus of human cytochrome b5, PAISAVAVALMYRLYMAED (shown as SEQ ID NO:6).

The C-terminus sequence of human cytochrome b5 can act as a membrane anchor, i.e. it can provide for attachment of human cytochrome b5 and other proteins to membranes. Hence, in some embodiments, the 37 amino acids of the C-terminus of human cytochrome b5 (SEQ ID NO:7) can be used to provide attachment to a membrane. In other embodiments, the 19 amino acids of the C-terminus of human cytochrome b5 (SEQ ID NO:6) can be used to provide attachment to a membrane. The attachment of these sequences or their variants to membranes is spontaneous. Once the carboxy sequence is in contact with the membrane, it spontaneously attaches to the membrane and thus becomes a membrane anchor. A polypeptide that includes at least one of these C-terminus sequences thus becomes spontaneously attached to a membrane. When attachment to a membrane is necessary for functionality of the protein, inclusion of the above C-terminus sequences to polypeptides should provide anchoring of such polypeptides to membranes.

One advantage of the present invention is that attachment of the expressed membrane anchor::polypeptide(s) to desired membrane(s) can be performed at various times post-expression of the protein. After the fusion protein is expressed, the fusion protein can be maintained in solubilized form for an extended period of time, and the linker can be cleaved whenever desired, to allow association of the membrane anchor:: polypeptide(s) to membranes). The linker can thus be cleaved, and the soluble membrane protein can be liberated, immediately after expression of the fusion protein, or at any desired time after expression of the fusion protein, for example after a period of storage, after a desired change in the reaction conditions, and at any other point in time etc. In various embodiments, the linker can thus be cleaved any desired time after the expression of the fusion protein, e.g. as a co-translational event along with expression of the fusion protein or at any subsequent time duration including at least one second, one minute, one hour, one day, one week, one month, or one year after the expression of the fusion protein. Once the linker is cleaved, the soluble membrane protein can then, via its membrane anchor, spontaneously associate with desired membranes. Therefore, the expression of the fusion protein and the cleavage of the linker may be temporally separated from each other.

"Maltose Binding Protein (MBP)" is a part of the maltose/maltodextrin system of *Escherichia coli*, which is responsible for the uptake and efficient catabolism of maltodextrins. For a recent review on MBP see Boos and Shuman, 1998, *Microbiol. Molec. Biol. Rev.* 62: 204-229.

Inclusion or addition of any one of the desired C-terminus sequences of the present invention to a polypeptide can be performed in a variety of ways known in the arts of molecular biology, genetic engineering, and biochemistry. It is known in the art how to artificially generate desired termini in proteins. Modification or design of the carboxy-terminus of a protein can also be accomplished at the genetic level. Conventional techniques of site-directed mutagenesis for addition or substitution of appropriate codons to the end of an isolated or synthesized gene can be employed to provide a desired amino-terminal structure for the encoded protein. Existing proteins can be modified, their carboxy termini can be mutagenized, or desired carboxy termini sequences of the present invention can be added to the proteins. For example, U.S. Pat. No. 5,132,213, incorporated herein by reference, describes a method of designing or modifying protein structure at the protein or genetic level to produce specified aminotermini. A desired carboxy terminus can be synthesized in vitro, and can then be fused to a desired polypeptide for subsequent expression and attachment to membranes.

In some examples, it is possible to use as a membrane anchor for polypeptides the C-terminus of approximately 37 amino acids of human cytochrome b5, as shown in SEQ ID NO:7. It is possible to modify one or more amino acids of this 37 amino acid C-terminus and use that modified sequence as a membrane anchor, and thus obtain functional homologs that can be used for practicing the present invention. A "functional fragment" or "functional equivalent" or "functional homolog" of the C-terminus sequences of the present invention is an amino acid sequence that is homologous to the specified C-terminus sequence but has one or more amino acid differences from the specified C-terminus sequence. A functional fragment or equivalent of a polypeptide retains at least some, if not all, of the activity of the specified C-terminus sequence. Hence, one or more conservative substitutions, deletions, insertions, or modifications may be introduced anywhere in this sequence (SEQ ID NO:7), and that modified sequence can then be added to desired polypeptides in order to serve as a membrane anchor and to provide attachment of the polypeptides to desired membranes or membrane vesicles. In some examples, the C-terminus of approximately 19 amino acids of human cytochrome b5, as shown as SEQ ID NO:6, can be used. Similarly, it is also possible to modify one or more amino acids of this 19 amino acid C-terminus and use that modified sequence as a membrane anchor. One or more conservative substitutions, deletions, insertions, or modifications may be introduced anywhere in this sequence (SEQ ID NO:6), and that modified sequence can then be added to desired polypeptides in order to serve as a membrane anchor and to provide attachment of the polypeptides to desired membranes or membrane vesicles.

Thus, it is contemplated that the compositions and methods of the present invention include C-terminus sequences that are at least 80%, preferably at least 85%, more preferably at least 90%, and more preferably at least 95% identical to the amino acid sequence of SEQ ID NO:7. As well, it is contemplated that the compositions and methods of the present invention include C-terminus sequences that are at least 80%, preferably at least 85%, more preferably at least 90%, and more preferably at least 95% identical to the amino acid sequence of SEQ ID NO:6.

Once a desired membrane anchor sequence from the C-terminus sequence of human cytochrome b5 is chosen, this membrane anchor sequence can be attached to a variety of proteins. Attachment of this membrane anchor can be performed through standard genetic engineering techniques. The membrane anchor can be attached at the C-terminus of a protein. Examples of variations in amino acids that can be attached to the C-terminus with differing ability to spontaneously direct a polypeptide sequence into a membrane are known (Brambillasca et al., 2006, *J. Cell Biology* 175: 767-777). Alternatively, the membrane anchor can be attached at the N-terminus of a protein. Examples of variations in amino acids that can be attached to the N-terminus with differing ability to spontaneously direct a polypeptide sequence into a membrane are known (Nessa et al., 2005, *Nature* 433: 377-381). It is also possible to insert the membrane anchor anywhere in the protein sequence, i.e. approximately at the beginning, middle, or end of the protein. More than one membrane anchor can be attached to a protein sequence. When more than one membrane anchor is attached to a protein sequence, the membrane anchors may be identical. Alternatively, the membrane anchors may differ from each other, i.e. they may have different lengths, different amino acid sequences, or both different lengths and different amino acid sequences.

The methods of the present invention can be practiced in a variety of ways. Suitable examples for practicing the methods include expression of one or more components of the present invention using cell-free translation systems. For cell-free translation, messenger RNA molecules encoding the fusion protein under control of the appropriate promoters are provided to the cell-free translation extract. Factors that remove the membrane protein from the fusion by acting on the linker can be added directly to the cell-free translation reaction, or can be added at any later time during the expression of the fusion protein. If the factors are added along with lipids, liposomes, or microsomes, the liberated membrane protein will be spontaneously transferred into the lipid phase. Alternatively, the factors can be added at any subsequent time after expression of the fusion protein. Typically, the cell-free translation is performed in test tubes, in multi-well configuration, in small or large-scale reactors, or in automated robotic equipment using methods that are well known and commonly employed in the art (Vinarov et al., 2006, *FEBS J.* 273:4160-4169).

The fusion protein can also be produced in cellular expression hosts such as *Escherichia coli, Saccharomyces cerevisiae*, or other expression hosts known. The membrane protein can be liberated in situ by providing suitable factors in the cellular hosts. Alternatively, the fusion protein and any required factors can be prepared using standard purification procedures, and provided as purified components to practice the present invention. Typically release of the purified membrane protein from the fusion will be performed in vitro, in test tubes, in multi-well configuration, or in small or large-scale reactors in the presence of liposomes. Highly purified liposomes containing the entrailed membrane protein can be prepared using density gradient centrifugation methods that are well known and commonly employed in the art (Sobrado et al., 2008, *Protein Expr. Purif.* 58: 229-241).

The membrane polypeptides of the present invention may include one or more hydrophobic regions that allow association of the membrane proteins with the membrane. The membrane polypeptides may be monotopic membrane proteins. Alternatively, the membrane proteins may be polytopic membrane proteins. One or more of these hydrophobic regions may include the membrane anchors of the present invention, i.e. they may include one or more C-terminus sequences as described herein.

"Membrane protein" or "membrane polypeptide" or "membrane-bound protein" for the purpose of this invention refers to a protein or a polypeptide molecule that is attached to, anchored to, or associated with, the membrane of a cell or an organelle. A membrane protein can have a hydrophobic region that allows association of the protein with a membrane. Membrane proteins often serve as receptors or provide channels for polar or charged molecules to pass through the cell membrane. Examples of membrane-bound proteins include integral membrane proteins (permanently attached to the membrane), transmembrane proteins (span the membrane), peripheral membrane proteins (temporarily attached to the lipid bilayer or to integral membrane proteins by a combination of hydrophobic, electrostatic, and other non-covalent interactions), integral monotopic proteins (permanently attached to the membrane from one side), structural membrane-anchoring polypeptides, membrane-bound polypeptides that can form transmembrane channels, and the like. Some of these are described in *Protein-Lipid Interactions*, 2005, Tamm, ed., Wiley-VCH, Weinheim, Germany; and in Popot and Engelman, 2000, *Annu. Rev. Biochem.* 69: 881-922.

A "system for expressing a membrane polypeptide (or protein)" or a "system for expressing a functional membrane polypeptide (or protein)" refers to three or more components that are mixed together in order to facilitate the expression of a membrane polypeptide (or protein) and its attachment to a membrane, where the membrane polypeptide (or protein) can be functional. Such components may include, e.g., solubilizing agents, linkers, membrane proteins, and others. These components can be suitably cloned into an expression vector, e.g. into the *E. coli* expression vector pQE-80L (Qiagen Inc., Valencia, Calif.).

The systems of the present invention may further include other components such as proteinaceous or non-proteinaceous molecules that are involved in cleavage of fusion proteins and attachment of membrane proteins to membranes. These components may interface together. The components of the systems may be structurally or functionally related.

The proteins of the present invention may include affinity purification tags. "Affinity purification tag" refers to a peptide or polypeptide tag that can be appended to recombinant expressed proteins. Affinity purification tags have traditionally been used as a way of purifying proteins using standard conditions rather than developing individual biochemical purifications based on each protein's physical characteristics. More recently, their role as an aid to solubilization of a fusion partner has been exploited. Affinity purification tags have been described, e.g., in the design of high-throughput methods of protein production for structural biology (Stevens, 2000, *Structure* 8: R177-R185). Examples of fusion tags used in recombinant protein expression and purification include: His-tag (with a typical size of 6, 8, or 10 amino acids); T-7 tag (with a typical size of 11 or 16 amino acids); S-tag (with a typical size of 15 amino acids); FLAG™ peptide (with a typical size of 8 amino acids); thioredoxin (with a typical size of 109 amino acids); His-patch thioredoxin (with a typical size of 109 amino acids); lacZ (β-Galactosidase); chloramphenicol acetyltransferases; trpE; avidin/streptavidin/Strep-tag; staphylococcal protein A; streptococcal protein G; glutathione-S-transferase (GST); dihydrofolate reductase (DHFR); cellulose binding domains (CBDs); maltose binding protein (MBP); galactose binding protein; calmodulin binding protein (CBP); HSB-tag; ubiquitin; and others. Combinations of two or more affinity purification tags can also be used.

To facilitate purification of the expressed proteins, suitable tags may be genetically engineered. In some embodiments, to facilitate purification of the encoded proteins by metal ion affinity chromatography, a cleavable $His_6$ tag or other affinity purification tags can be engineered in the expression vector, for example at the start of the cloned cDNAs. If desired, authenticity of the cloned fragments can be confirmed by DNA sequencing using vector-specific primers.

This invention provides an improved formulation of cytochrome b5 that can be used as a research tool or for diagnostic purposes. The cytochrome b5 produced according to the methods of the present invention is functional; it can incorporate the heme, and it spontaneously attaches to membranes. "Functional" substance refers to a substance that has an effect on the metabolic activity of living cells. "Functional membrane polypeptide" refers to a polypeptide that is attached to a membrane and that can perform a particular biological activity or a function. For example, in contrast to soluble forms of cytochrome b5, when cytochrome b5 is attached to a membrane it can have a particular biological activity or a function (see Table 1). "Functional cytochrome b5" refers to cytochrome b5 that has incorporated heme, and that can further be attached to a biological membrane, where it can be functional, e.g. it can be a suitable substrate for cytochrome b5 reductase. Nucleic acid and amino acid sequences of human cytochrome b5 are disclosed in U.S. Pat. Nos. 5,831,018 and 6,083,704, both of which are incorporated herein by reference.

The present invention provides methods and compositions that result in a novel, simpler way of overproducing and purifying cytochrome b5. In one embodiment, this new methods involve making a fusion of cytochrome b5 to maltose binding protein (MBP). The purified fusion protein, unlike previous methods of synthesizing cytochrome b5, is soluble in aqueous solution, does not require reconstitution, refolding, or reassociation with the co-factor heme. Moreover, the fusion protein is highly stable, and it is a suitable substrate for cytochrome b5 reductase, meaning that it retains its functionality (biological activity), in particular its recognition properties. In one embodiment, simple proteolytic cleavage can be used to release the MBP moiety to allow cytochrome b5 to associate with membranes in activity assays. This fusion protein represents an improvement over native cytochrome $b_5$ for users who want to perform desaturase or other assays requiring membrane association. The fusion can be left as is until just prior to use.

A "protein assay" refers to a standard laboratory method for measuring protein activity.

In one embodiment, the present invention provides a method that permits heterologous expression and purification of active full-length human cytochrome $b_5$. The human cytochrome b5 containing the essential C-terminal membrane binding sequence is expressed as a highly soluble fusion protein. Stoichiometric incorporation of protoporphyrin IX is accomplished by bacterial expression in auto-induction medium without addition of heme to the medium. The fusion protein can be purified to homogeneity as a soluble enzyme by use of chromatographic methods, with full retention of the heme prosthetic group. The full-length human cytochrome $b_5$ can be released from the fusion protein by site-specific proteolysis and will spontaneously associate with membrane lipids. The membrane-associated, functional full-length form of human cytochrome b5 can find utility in a variety of in vitro assays, e.g. in studies of the function of enzyme complexes such as stearoyl-CoA desaturase and cytochrome P450.

These methods find utility as an in situ delivery method for production and incorporation of membrane proteins, allowing conducting functional studies at a desired time. The membrane proteins can be, for example, monotopic membrane proteins.

In one embodiment of this invention, in contrast to existing methods, the methods described herein encompass a way to make large quantities of the homogeneously pure full length cytochrome b5 (fl-cytb5) with full incorporation of heme. The fusion protein has full catalytic activity with human cytochrome b5 reductase. Thus, the methods of the present invention can be used as a way to prepare and store the cytochrome b5 as a soluble fusion protein without the addition of contaminating detergents and to later liberate the protein in situ in the presence of a membrane or a membrane fraction without introducing contaminating detergents. fl-cytb5 is used in a number of important enzymatic reactions as a specific electron donor (with roles, e.g., in androgenesis, fatty acid biosynthesis, reduction of cytochrome P 450, reduction of hemoglobin, etc.; see Table 1). The methods described herein allow controlled introduction of this protein into membrane environments containing medically relevant enzymes such as stearoyl-CoA Δ9 desaturase or several cyt P450s involved in drug metabolism.

As supporting evidence for the utility of the new method, the inventors discovered that expression of the human cytochrome b5 by itself from the same expression vector gives only an insoluble protein that lacks heme. Although it was previously known that this protein could be purified and reconstituted with heme, this is a slow, inefficient process requiring protein refolding, heme incorporation and detergent solubilization. None of these handling steps are required with the disclosed methods of the present invention.

In the fusion proteins of the present invention, the solubilizing agent can be any one of a number of known solubilizing proteins, including but not limited to: (i) maltose binding protein (MBP) (Pryor and Leiting, 1997, *Protein Exp. Purif.* 10: 309-319); (ii) thioredoxin (TRX) (Holmgren, 1989, *J. Biol. Chem.* 264: 13963-13966); (iii) glutathione S-transferase (GST) (Nygren et al., 1994, *Trends Biotechnol.* 12: 184-188; (iv) lysozyme; (v) trigger factor, a molecular chaperone that is present in eubacteria (Ludlam et al., 2004, *Proc. Natl. Acad. Sci. USA* 101: 13436-13441), which is a soluble protein that folds precursor proteins into a membrane-assembly-competent form (Crooke and Wickner, 1987, *Proc. Natl. Acad. Sci. USA* 84: 5216-5220); (vi) Protein A (Samuelsson et al., 1994, *Biochemistry* 33: 4207-4211); (vii) ubiquitin (Power et al., 1990, *J. Biol. Chem.* 265: 1419-1424); (viii) DsbA (Zhang et al., 1998, *Protein Exp. Purif.* 12: 159-165), and others. However, it is possible that some of these proteins may have less efficiency as solubilizing agents in comparison to MBP (Kapust and Waugh, 1999, *Protein Sci.* 8: 1668-1674). Indeed, the inventors compared the ability of three soluble fusion partners—maltose binding protein (MBP), glutathione S-transferase (GST), and thioredoxin (TRX)—to inhibit the aggregation of six diverse proteins that normally accumulate in an insoluble form. MBP was a far more effective solubilizing agent than the other two fusion partners. Unexpectedly, the inventors discovered that fusion of a target protein to MBP was able to promote the proper folding of the target protein into its functional conformation. Thus, MBP seems to be capable of functioning as a general molecular chaperone in the context of a fusion protein.

In one embodiment, the invention contemplates integration of a protease into the recombinant expression cassette that is used for expression of the fusion protein, albeit under a relatively weak promoter. Thus, when the protein is expressed, the protease is also made; the protease then acts as a cleaver, cleaves with specificity at the right place (i.e. the linker), thereby releasing the membrane protein. One skilled in the art will be able to determine how much protease is need for cleavage, its specificity, etc., in order to obtain the desired specific cleavage and efficiency of cleavage. For example, tobacco etch virus (TEV) protease can be used; TEV protease is a slow, yet highly specific protease. The human rhinovirus 3C protease can also be used; it is a faster protease, yet a little bit less specific. The tobacco vein mottling virus (TVMV) protease can be used to obtain desired, specific cleavage, according to the methods of the present invention. In addition, combinations of more two or more proteases such as those described above, or additional ones, can also be used for cleavage of the expressed fusion protein. Methods of measuring protease activity are known in the art, e.g. as described in U.S. Patent Application Publication No. US2005/0227306 A1, which is incorporated herein by reference.

In one embodiment, the present invention provides genetically engineering a system for the in vitro expression of polypeptides that are attached to membranes, i.e. membrane proteins or membrane-attached proteins. The systems of the present invention may include increasing the biological activity, i.e. the functionality of the expressed membrane proteins.

In one embodiment, the present invention provides for the use of the C-terminal signal sequence of cytochrome b5 for the direction of other proteins to a liposome. Using the methods described herein, it is possible to express pure proteins that are stable and storable in large quantities that can be prepared with liposomes at one's convenience, at a cost significantly lower in comparison to current methods.

In some embodiments, different variants of the genes or proteins are introduced. These include homologs, mutants, proteins with amino acids substitutions, etc., depending on the objective of the investigation. In addition, recombinant fusion proteins of this invention can be expressed after codon optimization is performed. For example, the cytb5-sd has been expressed in *E. coli* from codon-optimized genes (von Bodman, et al., 1986, *Proc. Natl. Acad. Sci. USA* 83: 9443-9447).

In one embodiment, the expression of fusion proteins of the present invention is achieved through the use of vectors such as plasmids, phages, phagemids, viruses, artificial chromosomes, and the like. Preferred vectors are expression vectors. Expression vectors contain a promoter that may be operably linked to a coding region. A gene or coding region is operably linked to a promoter when transcription of the gene initiates from the promoter. More than one gene may be operably linked to a single promoter. In one embodiment of the present invention, at least one MBP gene and at least one cytochrome b5 gene are both operably linked to the same promoter, so that they are expressed in frame as a MBP::cytochrome b5 fusion protein. In another embodiment of the present invention, at least one MBP gene and at least one cytochrome b5 gene are both operably linked to the same promoter, however an additional linker domain is inserted in frame between the MBP gene and the cytochrome b5 gene, so that they are expressed as a MBP::linker::cytochrome b5 fusion protein (Sobrado et al., 2008, *Protein Expr. Purif.* 58: 229-241). The vector can be introduced into an organism that is suitable for expression of the fusion proteins of the present invention.

A variety of expression vectors may be used for expression in *E. coli*, insect, yeast, or mammalian cells. Expression vectors that may be used include, but are not limited to, the Gateway® Destination vectors (Invitrogen, Carlsbad, Calif.), pQE-30, pQE-40, and pQE-80 series (Qiagen, Valencia, Calif.), pUC19 (Yanisch-Perron et al., 1985, *Gene* 33: 103-119), pBluescript II SK+ (Stratagene, La Jolla, Calif.), the pET system (Novagen, Madison, Wis.), pLDR20 (ATCC 87205), pBTrp2, pBTac1, pBTac2 (Boehringer Ingelheim Co., Ingelheim, Germany), pLSA1 (Miyaji et al., 1989, *Agric. Biol. Chem.* 53: 277-279), pGEL1 (Sekine et al., 1985, *Proc. Natl. Acad. Sci. USA.* 82: 4306-4310), and pSTV28 (manufactured by Takara Shuzo Co., Japan). When a yeast strain is used as the host, examples of expression vectors that may be used include pYEST-DES52 (Invitrogen), YEp13 (ATCC 37115), YEp24 (ATCC 37051), and YCp50 (ATCC 37419). When insect cells are used as the expression host, examples of expression vectors that may be used include pVL1393 (BD Biosciences, Franklin Lakes, N.J.) and pIEX (Novagen).

In some embodiments, vectors such as pVP55A and pVP56K can be used for practicing the methods of the present invention. These vectors were created from pQE80 (Qiagen) as described below. Vectors pVP55A and pVP56K are part of a platform developed to support high-throughput structural biology studies. Their modular design allows systematic variation of promoters, selectable markers, fusion tags, and patterns of either in vivo or in vitro proteolysis of the fusion proteins. These vectors also allow high-fidelity transfer of cloned and sequence-verified genes between different expression contexts for both bacterial and wheat germ cell-free translation. Thus, the present invention contemplates the use of His8- and His8-MBP as vehicles for expression and purification of functional membrane polypeptides, such as, for example, the monotopic membrane protein human cytochrome b5 which retains the functionally significant membrane anchor domain at the carboxy terminus. This is a different use for MBP that was originally envisaged by others, e.g. Kapust and Waugh, 1999, *Protein Sci.* 8: 1668-1674.

It is further possible to optimize the fusion protein expression system of this invention by stabilizing each of the components of the expression system in its own stabilizing buffer, using methods known in the art.

The 19 amino acids long C-terminal sequence, which serves as a membrane anchor sequence, is shown as SEQ ID NO:6.

The 37 amino acids long C-terminal sequence, which serves as a membrane anchor sequence, is shown as SEQ ID NO:7. It includes the 19 amino acid long sequence shown in SEQ ID NO:6.

The amino acid sequence of the His8-MBP-fl-cytb5 fusion protein is 538 amino acids long, and is shown as SEQ ID NO:8.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. It is also to be understood that the terminology used herein is for the purpose of describing particular embodiments only, and is not intended to limit the scope of the present invention, which is limited only by the claims. The following examples are offered to illustrate, but not to limit the claimed invention.

Example 1

Materials

Unless otherwise stated, bacterial growth reagents, antibiotics, routine laboratory chemicals, and disposable labware were from Sigma-Aldrich (St. Louis, Mo.), Fisher (Pittsburgh, Pa.), or other major distributors. Chloroporphyrin IX was obtained from Sigma-Aldrich. DNA sequencing was performed in the University of Wisconsin Biotechnology Center.

Expression Vectors

The expression vectors pVP55A and pVP56K were created from pQE80 (Qiagen) by removal of a non-functional chloramphenicol acetyltransferase coding region and specifically in pVP56K by replacement of the beta-lactamase coding region with an aminoglycoside 3'-phosphotransferase coding region conferring kanamycin resistance. The vectors use the viral T5 promoter under control of an engineered double lac operator for recombinant gene expression. The plasmid backbones also provide the strong lacI$^q$ promoter for elevated expression of the lac repressor, LacI. Elevated expression of LacI provides strong attenuation of basal expression. Other design features of the expression plasmids and examples of their use are reported elsewhere (Blommel et al., 2006, *Protein Expr. Purif.* 47: 562-570).

Vector pVP55A can be used to add an N-terminal tag of His8 to the target protein, i.e., to the functional membrane polypeptide to be expressed; vector pVP56K can be used to add an N-terminal tag of His8-maltose binding protein. The linker region between the tag and the functional membrane polypeptide (target protein) contains the recognition sequence for site-specific tobacco etch virus (TEV) protease (Blommel and Fox, 2007, *Protein Expr. Purif.* 55: 53-68).

Cloning

The gene for fl-cytb5 from human (accession number: BC015182; originally cloned from the Mammalian Gene Collection; Strausberg et al., 1999, *Science* 286: 455-457) was obtained from Open Biosystems (Huntsville, Ala.). The gene was amplified using the forward primer 5'-TTCGG CGATCGCCGAAATGGCAGAACAAAGCGAC-3' (SEQ ID NO:1) containing an SgfI restriction site (underlined) and the reverse primer 5'-AGCA GTTTAAACTTAGTCCTCTGCCATGTATAGGCG-3'(SEQ ID NO:2) containing a PmeI restriction site (underlined).

expression of the soluble form of human cytb5 reductase as a fusion to an N-terminal His8 tag (His8-cytb5R).

Schematic representations of the fusion protein constructs are shown in FIG. 1C and results from their use are summarized in Table 2.

TABLE 2

Vectors and expressed proteins

| Vector | Expressed protein[a] | Expression medium | Cell yield[b] g/L | Purified protein yield[c] mg/g | Cofactor incorporation[d] |
|---|---|---|---|---|---|
| pVP55A | His8-cytb5-sd | Auto-induction | 25[e] | 0.6 | Yes, high |
| pVP55A | His8-fl-cytb5 | Auto-induction | 12 | >1[b] | No, insoluble |
| pVP56K | His8-MBP-fl-cytb5 | Auto-induction | 12 | 0.42[c] | Lost in purification |
| pVP56K | His8-MBP-fl-cytb5 | TB-IPTG | 3 | 0.42 | Lost in purification |
| pVP55K | His8-cytb5R | Auto-induction | 25[e] | 0.6 | Yes, high |

[a]Schematic representations of the expressed proteins are shown in FIG. 1C.
[b]Wet cell weight obtained per liter of culture medium after preparative centrifugation as described in Examples section.
[c]Amount of purified protein obtained per gram of wet cells.
[d]Protoporphyrin IX in cytb5 variants; FAD in His8-cytb5.
[e]From 10 liter fermentation.

The SgfI and PmeI restriction sites were used for Flexi Vector cloning (Promega, Madison, Wis.) as previously described (Blommel, 2006, *Protein Expr. Purif.* 47: 562-570). Transfer of the amplified fl-cytb5 gene into pVP55A gave a vector for expression of His8-fl-cytb5. Transfer of the same amplified gene into pVP56K gave a vector for expression of the fusion protein His8-MBP-fl-cytb5.

A linear restriction enzyme map of the pVP56K expression vector is shown in FIG. 1A. The amino acid sequence of the His8-MBP-fl-cytb5 is shown in FIG. 1B; the His8 tag and the first five fl-cytb5 residues liberated by TEV proteolysis are shown in bold letters, the TEV protease cleavage site is shown in italic letters, and the C-terminal membrane anchor domain is underlined. FIG. 1C schematically illustrates example of generated fusion proteins.

The cytb5-sd was obtained by removal of the 37-residue C-terminal membrane anchor sequence (SEQ ID NO:7) from the full-length cytb5, using PCR amplification. The forward primer was the same as that used for cloning the full-length protein (SEQ ID NO:1), while the reverse primer was 5'-AGCA GTTTAAACTTACGGTTCCGGCGGTTTGTTCAG-3' (SEQ ID NO:3) (PmeI site underlined). The amplified gene encoded the 97 amino acids from the N-terminal soluble domain that contains the heme binding region. This amplified gene was transferred into pVP55A so that His8-cytb5-sd could be generated.

The human cytochrome b5 reductase gene (GenBank accession number: BC004821) was obtained from Open Biosystems (Huntsville, Ala.) and amplified using the forward primer 5'-TTCGG CGATCGCCATGAAGCTGTTCCAGCGCTCCACG-3'(SEQ ID NO:4) and the reverse primer 5'-TCGT GTTTAAACTCAGAAGACGAAGCAGCGCTC-3'(SEQ ID NO:5) (5' SgfI and 3' PmeI sites underlined). The amplified gene encodes a 23-residue deletion corresponding to the N-terminal membrane-binding residues (Spatz and Strittmatter, 1971, *Proc. Natl. Acad. Sci. USA* 68: 1042-1046). Transfer of the amplified gene into pVP55A gave a vector for Expression and Purification of fl-cytb5

Vectors pVP55A-fl-cytb5 and pVP56K-fl-cytb5 (Table 2) were individually transformed into *E. coli* BL21. For scale-up, a 10 mL culture was inoculated with a single colony from freshly transformed cells and incubated overnight in the non-inducing version of auto-induction medium (Blommel et al., 2007, *Biotechnol. Prog.* 23: 585-598). The overnight scale-up culture was added to 1 L of auto-induction medium containing either 200 μg/mL of ampicillin (pVP55A) or 50 μg/mL of kanamycin (pVP56K). The growth and expression were continued for approximately 24 h at 25° C. Cells were harvested by centrifugation at 5,000×g for 30 min. The pVP55A-fl-cytb5 cells had no distinct color, while the pVP56K-fl-cytb5 cells were bright red in color. The yield of wet cell paste from 1 L of auto-induction medium was typically approximately 12 g (Table 2).

Cells transformed with pVP56K-fl-cytb5 were also grown at 37° C. in Terrific Broth medium until the $OD_{600}$ reached approximately 0.6, isopropyl-β-D-1-thiogalactopyranoside (IPTG) was added to a final concentration of 0.5 mM, and the temperature was dropped to 25° C. After 4 h, the cells were harvested by centrifugation at 3000×g and stored at −80° C. The cells had no distinct color. The yield of wet cell paste from 1 L of IPTG induction medium and short time expression was typically approximately 4 g.

The His8-MBP-fl-cytb5 was purified by Ni immobilized metal chromatography (IMAC). The cell pellet (approximately 12 g) was re-suspended in 50 mL of 25 mM HEPES pH 7.5, 20 mM imidazole, 500 mM NaCl, and 25 mg each of lysozyme, DNase, and RNase. The cell suspension was stirred for 20 min at 4° C., followed by sonication for a total of 2 min with 10 s pulses. Insoluble proteins and cell debris were pelleted by centrifugation at 39,000×g for 1 h. The supernatant was loaded onto a 5-mL His Trap fast flow column (GE Healthcare, Piscataway N.J.) equilibrated with 25 mM HEPES, pH 7.5, 20 mM imidazole, and 500 mM NaCl and washed with the same buffer until the $OD_{280}$ reached baseline levels. The bound protein was eluted from a gradient of 20 to 300 mM imidazole. Peaks containing the fusion protein were detected at ~100 mM imidazole and ~180 mM imidazole. The pooled fractions were concentrated by ultrafiltration using a YM30 membrane (Millipore, Bedford Md.). Imidazole was removed from the sample by dialysis against 25 mM HEPES, pH 7.5, 100 mM NaCl. For short-term storage (several weeks), the dialysis buffer was amended to contain 10% (v/v) glycerol and the protein was stored at 4° C. For long-term storage, the glycerol-amended His8-MBP-fl-cytb5 could also be drop frozen in liquid $N_2$ and stored at −80° C.

Incorporation of Heme into His8-MBP-fl-cytb5

The preparation of hemin chloride solutions and the incorporation of heme into His8-MBP-fl-cytb5 were adapted from elsewhere (Mulrooney and Waskell, 2000, *Protein Expr. Purif.* 19: 173-178). Briefly, a 1-mL sample was prepared by 40-fold dilution of the purified, concentrated, and dialyzed His-MBP-fl-cytb5 into 20 mM Tris, pH 8.0, containing 1 mM EDTA. The absorbance spectrum of the sample was recorded from 250 to 600 nm on an Agilent 8453 UV-spectrophotometer (Santa Clara, Calif.). Aliquots (1 µL) of 0.85 mM hemin chloride were titrated into the sample and the absorbance spectrum was monitored. Incorporation was judged to be complete when an increase in absorbance at 385 nm and a shift in the Soret peak from 412 to 410 nm were observed. The amount of heme required to reconstitute the remainder of the purified sample was calculated based on the small-scale titration result. To verify that the observed spectral changes were not due to adventitious binding of heme to MBP, hemin chloride was also titrated into free MBP as previously reported (Kroliczewski et al., 2002, *Biochim. Biophys. Acta* 1598: 177-184).

Expression and Purification of cytb5-sd

The cytb5-sd was expressed using a 10 L fermenter. Vector pVP55A-cytb5-sd was transformed into *E. coli* BL21. A single colony was used to inoculate a 10 mL culture that was incubated overnight at 37° C. The entire culture was used to inoculate 1 L of Terrific Broth medium containing 200 mg of ampicillin. After approximately 12 h at 37° C., this culture was used to inoculate 9 L of auto-induction medium equilibrated at 25° C. in the fermenter vessel. After approximately 24 h, the cells were harvested by centrifugation at 5,000×g for 30 min using an Avanti J-HC centrifuge (Beckman Coulter, Fullerton Calif.) with a JS-42 rotor. In the fermenter, the yield of wet cell paste from 1 L of auto-induction medium was typically approximately 20 g. The pVP55A-cytb5-sd cells had a distinct red color. The cell paste was stored at −80° C.

The cell paste (approximately 20 g) was re-suspended, sonicated, centrifuged and separated by Ni IMAC as described above for fl-cytb5. A gradient of 20 to 300 mM imidazole was applied, and the bound cytb5-sd eluted from the Ni column at approximately 180 mM imidazole was concentrated and loaded into an Sephacryl S-100 column (5 cm inner diameter×80 cm length, GE Healthcare) equilibrated with 25 mM HEPES, pH 7.5, containing 100 mM NaCl. The fractions containing purified protein were identified by optical absorbance and denaturing gel electrophoresis.

Expression and Purification of Soluble His8-cytb5R

The soluble form of His8-cytb5R was expressed using a 10 L fermenter. Vector pVP55A-cytb5R was transformed into *E. coli* BL21(DE3). A single colony was used to inoculate a 10-mL culture and incubated overnight at 37° C. The entire culture was used to inoculate 1 L of Luria-Bertani medium containing 50 mg of kanamycin. After approximately 12 h at 37° C., this culture was used to inoculate 9 L of auto-induction medium equilibrated at 25° C. in the fermenter vessel. After approximately 24 h, the cells were harvested by centrifugation at 5,000×g. The cell paste was stored at −80° C.

The cell paste (approximately 20 g) was re-suspended, sonicated, centrifuged, and separated by Ni IMAC as described above for cytb5-sd. His8-cytb5R was >95% pure after this single step. The pure protein was pooled, concentrated using ultrafiltration (YM10, Millipore, Bedford Md.), and the buffer was exchanged by dialysis to 25 mM HEPES, pH 7.5, containing 100 mM NaCl. The purified His8-cytb5R was stored at −80° C.

Enzyme Activity Measurements

The reduction of the different cytb5 preparations by His8-cytb5R was measured at 25° C. by following the change in absorbance at 413 nm in an Agilent 8453 UV-visible spectrophotometer. The concentration of cytb5 was varied from 0.3 µM to 15 µM in 1 mL of 25 mM HEPES, pH 7.5, containing 1.3 nM of His8-cytb5R. The reaction was initiated by the addition of NADH to a final concentration of 100 µM. Initial rate data were analyzed by non-linear least squares fitting using Kaleidagraph (Synergy Software, Reading, Pa.) and the Michaelis-Menten equation $v=k_{cat}[S]/(K_M+[S])$. The concentrations of the cytb5 variants and cytb5R were determined by optical spectrometry using the extinction coefficients 117 $mM^{-1}$ $cm^{-1}$ at 412 nm and 11.3 $mM^{-1}$ $cm^{-1}$ at 466 nm, respectively (Estabrook and Werringloer, 1978, *Methods Enzymol.* 52: 212-220; Mihara and Sato, 1972, *J. Biochem.* 71: 725-725).

Liposome Preparation

Liposomes were prepared from 7.5 µmol of a lipid mix (85% 1-palmitoyl, 2-oleoyl phosphatidylcholine; 15% 1,2-dioleoyl phosphatidylserine, Avanti Polar Lipids, Alabaster, USA) labeled with 2 µCi of [$^3$H]-1,2-dipalmitoyl phosphatidylcholine (NEN, Cambridge, UK). The lipid mix was dissolved in chloroform (Burgess et al., 1991, *Biochemistry* 30: 4193-4200), the bulk of the organic solvent was removed by evaporation under a stream of $N_2$ gas, and the remaining trace level of chloroform was removed by incubation for 30 min under vacuum. The dried lipid film was re-hydrated with 20 mM HEPES, pH 7.4, containing 100 mM KCl for 30 min, vortexed for 5 min, and subjected to 5 freeze-thaw cycles. Liposomes were formed by extrusion from an Avanti mini-extruder using 11 passes through 100 nm track-etch polycarbonate membranes (Nucleopore, Pleasanton, Calif.).

In situ Delivery of fl-Cytb5 to Liposomes

TEV protease was expressed as an MBP fusion protein, liberated by auto-cleavage within the expression host, and purified as previously described (Blommel and Fox, 2007, *Protein Expr. Purif.* 55: 53-68). TEV protease reactions were conducted in 20 mM sodium phosphate, pH 7.0, containing 100 mM NaCl, 5 mM DTT, and 1 mM EDTA. For initial testing, aliquots of 10 µM His8-MBP-fl-cytb5 were digested with TEV protease at ratios of fusion protein to protease ranging from 200:1 to 10:1. At a ratio of 10:1, the proteolysis was complete in less than 30 min. Thus all the preparative protease reactions were done at this ratio for 30 min.

For the proteolysis reaction, His8-MBP-fl-cytb5 (10 µM), TEV protease (1 µM) and 45 µL of the liposome preparation described above were incubated with agitation at 37° C. in a total volume of 75 µL of 20 mM HEPES, pH 7.4, containing 100 mM KCl, 5 mM dithiothreitol, and 1 mM EDTA. After 30 min, the reactions were mixed 1:1 with 80% (w/v) Accudenz (Accurate Chemical and Scientific, Westbury N.Y.) made up in the same buffer used to perform the proteolysis. The mixture was transferred to Ultra-Clear centrifuge tubes (5 mm×41 mm, Beckman Coulter, Fullerton Calif.) and sequentially overlaid with 350 µL of 30% Accudenz followed by 100 µL of the reaction buffer. The mixture was centrifuged for 4 h at 45,000 rpm (189,000×g) and 4° C. in an L-60 ultracentrifuge (Beckman Coulter) using an SW-50.1 rotor with adaptors. After centrifugation, 60 µL fractions were collected from the top to the bottom of the gradient. Liposomes were detected by counting 5 µL of each fraction by liquid scintillation using an LS6500 counter (Beckman Coulter). An aliquot of 20 µL of 4×SDS-PAGE sample buffer was added to each fraction and 25 µL of the sample was loaded onto a Criterion SDS-PAGE polyacrylamide gel (4-20% gradient Tris-HCL, 1.0 mm, 26 comb, BioRad, Richmond Calif.) and analyzed as previously reported (Sreenath et al., 2005, *Protein Expr. Purif.* 40: 256-267).

Mass Spectral Analysis

TEV protease-treated samples of His8-MBP-cytb5 were analyzed by mass spectrometry at the University of Madison-Wisconsin Biotechnology Center. Purified protein samples were concentrated and desalted by acetone precipitation before addition (1:1) to an α-cyano-4-hydroxycinnamic acid matrix. MALDI-TOF analysis was performed with a 4800 MALDI TOF/TOF Analyzer from Applied Biosystems (Foster City, Calif.) calibrated with bovine serum albumin and deuterated bovine serum albumin.

Protein Expression

His8-cytb5-sd was highly expressed from pVP55A in both shaken flask culture and in a 10 L fermenter. This overexpression required neither codon optimization of the gene nor codon adaptation of the expression host. By using auto-induction medium in the 10 L fermenter, a typical yield of approximately 250 g of cell paste was obtained, and the cell paste had an intense red color.

FIG. 2 depicts images of results from Coomassie-stained denaturing gel electrophoresis. Lanes indicate: (1) 100 µg of purified cytb5-sd, where sd indicates the soluble domain; (2) 100 µg of purified His8-cytb5R, where R indicates the reductase protein; (3) molecular weight markers; (4) total cell lysate from *E. coli* cells expressing His8-MBP-fl-cytb5, where fl indicates the full-length protein; (5) insoluble fraction; (6) soluble fraction; (7) molecular weight markers; (8) soluble fraction from *E. coli* cells expressing His8-MBP-fl-cytb5; (9) His8-MBP-fl-cytb5 purified using Ni IMAC chromatography. As shown in FIG. 2, lane 1, purified His8-cytb5-sd could be obtained in >98% purity by the two-step purification.

His8-fl-cytb5 was also highly expressed from pVP55A (FIG. 2, lane 4), but accumulated entirely as an insoluble protein (compare lanes 5 and 6), and these cells had no distinct color. Since His8-fl-cytb5 was an insoluble apo-protein, it was not studied further.

His8-MBP-fl-cytb5 was also highly expressed from pVP56K in *E. coli*, but in this case, the fusion protein was entirely soluble (FIG. 2, lane 8), and the cells harvested from the auto-induction protocol were bright red. Interestingly, expression of His8-MBP-fl-cytb5 in Terrific Broth using a short time period induction with IPTG also gave strong expression of a soluble fusion protein (not shown), but these cells had no distinct color.

Protein Purification

The yields of purified His8-cytb5-sd and His8-MBP-fl-cytb5 are summarized in Table 2, and a summary of the purification of His8-MBP-fl-cytb5 is given in Table 3. All His8-tagged variants were purified using standard Ni IMAC to ~90% or greater purity as judged by denaturing gel electrophoresis.

TABLE 3

Purification of His8-MBP-fl-cytb5

| Step | Volume (mL) | Total protein (mg)[a] | Fold-purification |
|---|---|---|---|
| Sonicated cells[b] | 50 | 789 | 1 |
| Cell-free lysate | 41 | 571 | 1.4 |
| Ni-IMAC | 8.5 | 73[c] | 10.8 |

[a]Determined by Bradford assay (Bradford, 1976, Anal. Biochem. 72: 248-252).
[b]Prepared from 7.8 g of *E. coli* cells obtained from 2 L of IPTG-induced culture medium.
[c]Yield of His8-MBP-fl-cytb5 fusion protein. A yield of 18 mg of fl-cytb5 (25% of total protein yield) was present in the heme-reconstituted fusion protein as determined by optical spectroscopy. This measurement was consistent with the fraction of the 26% contribution of fl-cytb5 to the mass of the fusion protein.

During Ni IMAC purification of His8-MBP-fl-cytb5, two peaks that contained the fusion protein were detected from the gradient elution. Table 4 summarizes results of mass spectral analysis of these two peaks. The first peak from the IMAC column was redder colored than the second peak, and mass spectral analysis showed that the protein from this peak had a mass of 57648 Da, representing a loss of approximately 1980 Da from the mass of 59756 Da calculated for the complete fusion protein. In contrast, the second peak from the IMAC column had a mass of 59626 Da, which matched that calculated for the fusion protein within 0.17%. Thus it appears that the first peak contained a truncated form of cytb5 while the second peak contained the intact fusion protein, His8-MBP-fl-cytb.

FIG. 3 depicts an image of a Coomassie-stained SDS-PAGE gel showing differences in post-translational processing caused by long-term auto-induction or short-term IPTG induction. TEV proteolysis emphasizes the difference in size of the cytb5 variants, as illustrated in FIG. 3 by two distinct forms of cytb5 that were obtained after TEV proteolysis of the fusion protein.

TABLE 4

Mass spectral analysis

| Protein | Calculated mass | Observed mass (% difference from calculated mass) | Assignment |
|---|---|---|---|
| His8-MBP-fl-cytb5[a] | 59756 | | |
| Peak 1 | | 57648 (−3.5%) | C-terminal truncation[b] |
| Peak 2 | | 59626 (−0.2%) | His8-MBP-fl-cytb5 |
| His8-MBP-fl-cytb5[c] | 59756 | 59626 (−0.2%) | His8-MBP-fl-cytb5 |
| His8-MBP[d] | 43902 | 43898 (−0.01%) | His8-MBP |
| fl-cytb5[e] | 15715 | 15729 (+0.09%) | fl-cytb5 |

[a]From the auto-induction protocol. Peaks 1 and 2 were separated by gradient elution from Ni IMAC.
[b]Proposed to arise from deletion of the sequence PAISAVAVALMYRLYMAED (SEQ ID NO: 9) from the C-terminus of the fusion protein during auto-induction. The truncated fusion protein has a calculated mass of 57659, which is within −0.02% of the observed mass shown above.
[c]From the IPTG induction protocol.
[d,e]Proteins separated by treatment of His8-MBP-fl-cytb5 obtained from the IPTG induction protocol with TEV protease.

Since both peaks were purified using Ni IMAC and an imidazole gradient, it was unlikely that the N-terminus of the His8-MBP portion of the fusion protein was truncated. Instead, the mass of the smaller protein matched within 0.02% of the mass of 57659 Da calculated for removal of 19 residues from the C-terminus of cytb5 (corresponding to the sequence PAISAVAVALMYRLYMAED, see FIG. 1B and Table 4).

During Ni IMAC purification of His8-MBP-fl-cytb5 obtained from IPTG induction, a single peak that contained the fusion protein was detected from the gradient elution. Table 4 summarizes results of mass spectral analysis of this peak, and FIG. 3 shows that the predominant form after TEV protease treatment was fl-cytb5.

Spectral Properties of His8-MBP-fl-cytb5

Figure 4:
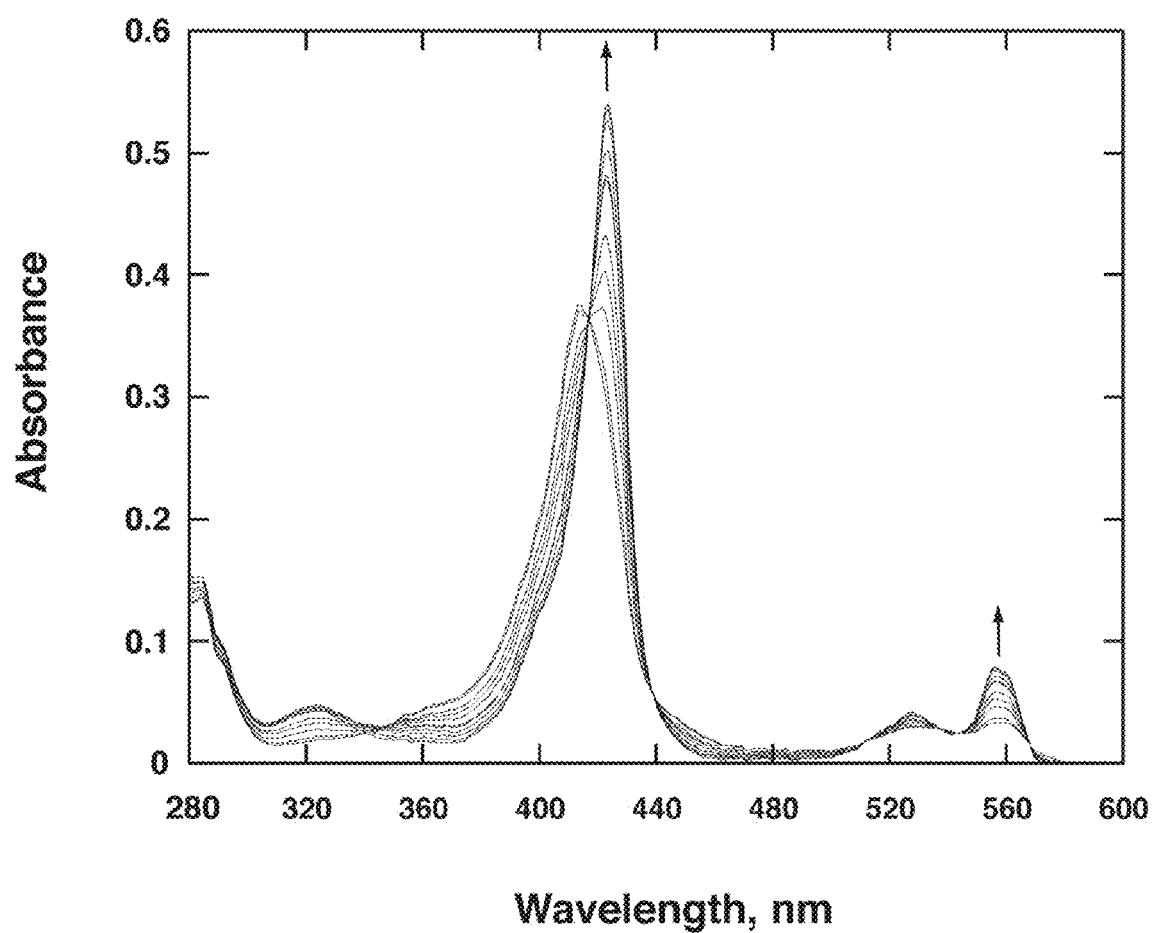
FIG. 4 is a graph showing optical spectra changes in His8-MBP-fl-cytb5 during a time-course reduction with soluble His8-cytb5R in the presence of NADH.

FIG. 4 is a graph showing optical spectra changes in His8-MBP-fl-cytb5 during a time-course reduction with soluble His8-cytb5R in the presence of NADH. As assembled, the reaction went to completion in about 30 seconds. A blank was obtained with buffer solution containing NADH. The spectral contributions of His8-cytb5R (1.3 nm) and NADH are negligible, as evidenced by isosbestic points at 420 and 438 nm.

Purified His8-MBP-fl-cytb5 has a Soret peak at 413 nm arising from the bis-imidazolate ligation of the ferric center in oxidized cytb5 (FIG. 4). Even though the cell paste obtained from auto-induction containing His8-MBP-fl-cytb5 was bright red, the purified protein obtained from Ni IMAC chromatography contained less than 10% of the heme content expected. Apparently, the high imidazole concentration required for elution of both bound forms of the fusion protein caused dissociation of the heme prosthetic group. In this case, the imidazole was removed from the protein preparation by dialysis, and the heme content was simply restored by titration with free heme as detected by a characteristic increase in Soret band absorbance (413 nm, 117 mM$^{-1}$ cm$^{-1}$, as compared to the 385 nm absorption maximum observed from free heme, 56 mM$^{-1}$ cm$^{-1}$). As previously reported (Kroliczewski and Szczepaniak, 2002, *Biochim. Biophys. Acta* 1598: 177-184), control experiments showed that titration of heme into preparations of His8-MBP did not give a shift in the heme optical spectrum. The heme-incorporated His8-MBP-fl-cytb5 preparation could be stored at 4° C. in buffer amended with 10% v/v glycerol for up to 2 months with no apparent deleterious effects as judged by catalytic properties, optical spectrum, and denaturing electrophoresis. Samples drop frozen in the amended buffer and stored at −80° C. for extended periods gave no change in these properties when thawed.

Interestingly, Ni IMAC was also used to purify His8-cytb5-sd, but in this case, the heme was retained in the purified protein to a high level upon the basis of the quantification of heme and protein and upon the lack of a diagnostic spectral shift when incubated with additional heme.

Purification and Characterization of His8-cytb5R

In these experiments, cytb5R was purified as a soluble N-terminal His8 fusion by using Ni IMAC. The protein obtained from the single step purification was >95% pure as judged by denaturing gel electrophoresis (FIG. 2, lane 2). The purified protein had an optical spectrum consistent with stoichiometric incorporation of FAD. Quantitative HPLC analysis also revealed high percentage incorporation of the cofactor in the purified protein.

His8-MBP-fl-cvtb5 is a Substrate for His8-cytb5R

His8-MBP-fl-cytb5 and His8-cytb5R were mixed in the presence of NADH in order to determine whether the fusion protein was recognized as a substrate by cytb5R. FIG. 4 shows that His8-MBP-fl-cytb5 was used by His8-cytb5R as an electron acceptor. Over an approximately 2 min period, the Soret peak was shifted from 413 nm to 423 nm and the peak at 555 nm increased in intensity. The resulting spectrum matched that of the reduced state of detergent-solubilized fl-cytb5. In control experiments, free heme was not reduced by His8-cytb5R in the time-scale and NADH concentration used for the cytb5 reduction.

Figure 5:
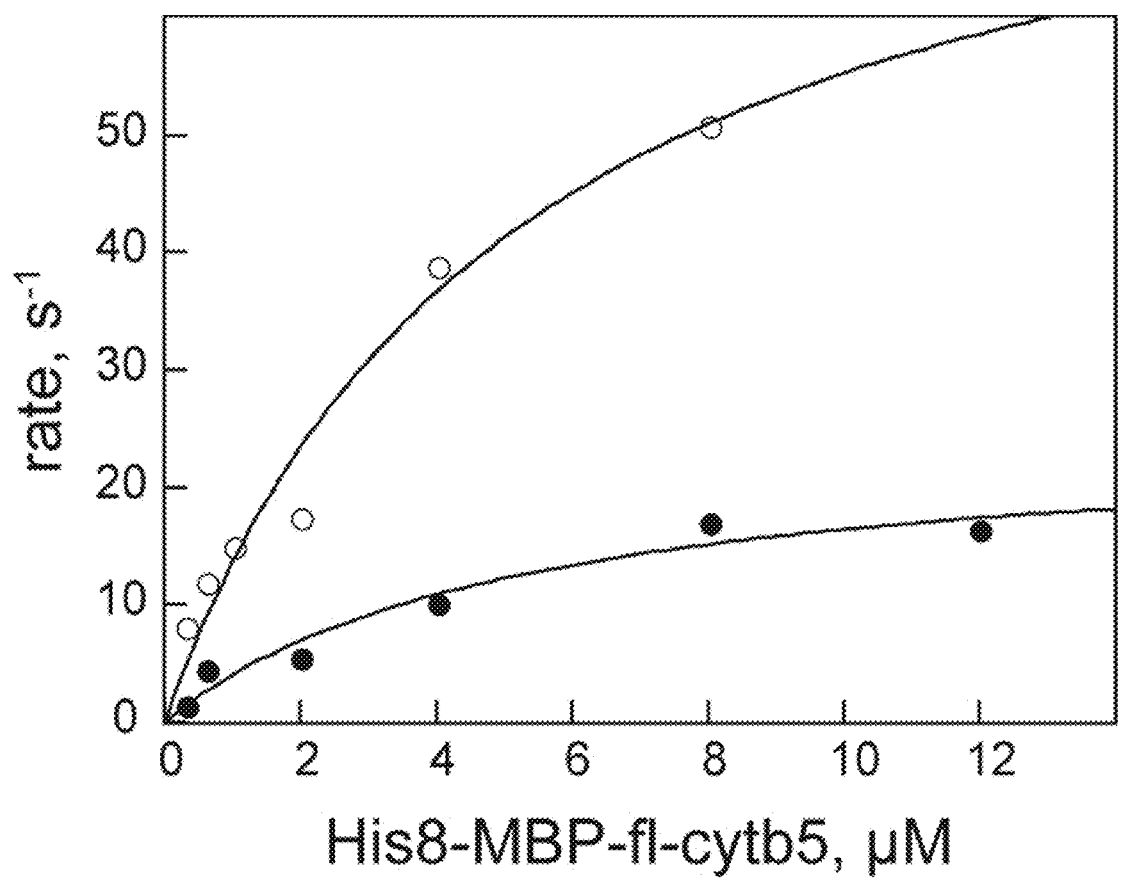
FIG. 5 is a graph showing steady-state reduction of His8-MBP-fl-cytb5 (○) and His8-cytb5-sd (●).

Steady-state kinetic parameters for reduction of both His8-MBP-fl-cytb5 and His8-cytb5-sd were determined in order to investigate the influence of the His 8-MBP fusion on the interactions between cytb5 and His8-cytb5R. FIG. 5 is a graph showing steady-state reduction of His8-MBP-fl-cytb5 (○) and His8-cytb5-sd (●). The lines are least square fits to the simple Michaelis-Menten assumption. FIG. 5 shows that both forms of cytb5 acted as saturable substrates for the electron transfer reaction, as the experimental data were well fit by the simple Michaelis-Menten equation (Table 5). The apparent $K_M$ values for both forms of cyt5 were the same. Interestingly, however, the His8-MBP-fl-cytb5 had an apparent $V_{max}$ that was ~3-fold higher than that of His8-cytb5-sd.

TABLE 5

Kinetic parameters for the reduction of cytochrome b5 variants by His8-cytochrome b5 reductase[a]

| Substrate | $V_{max}$, s$^{-1}$ | Km, μM | V/K, μM$^{-1}$ s$^{-1}$ | R |
|---|---|---|---|---|
| His8-MBP-fl-cytb5[b] | 84 ± 18 | 5 ± 2 | 17 ± 7 | 0.975 |
| His8-cytb5-sd[c] | 25 ± 5 | 5 ± 2 | 5 ± 2 | 0.977 |

[a]Reactions were performed as indicated above.
[b]Fusion protein from expression with pVP56K (FIG. 1A).
[c]cytb5 soluble domain from expression in pVP55A (FIG. 1C).

TEV Protease Reaction

Figure 6:
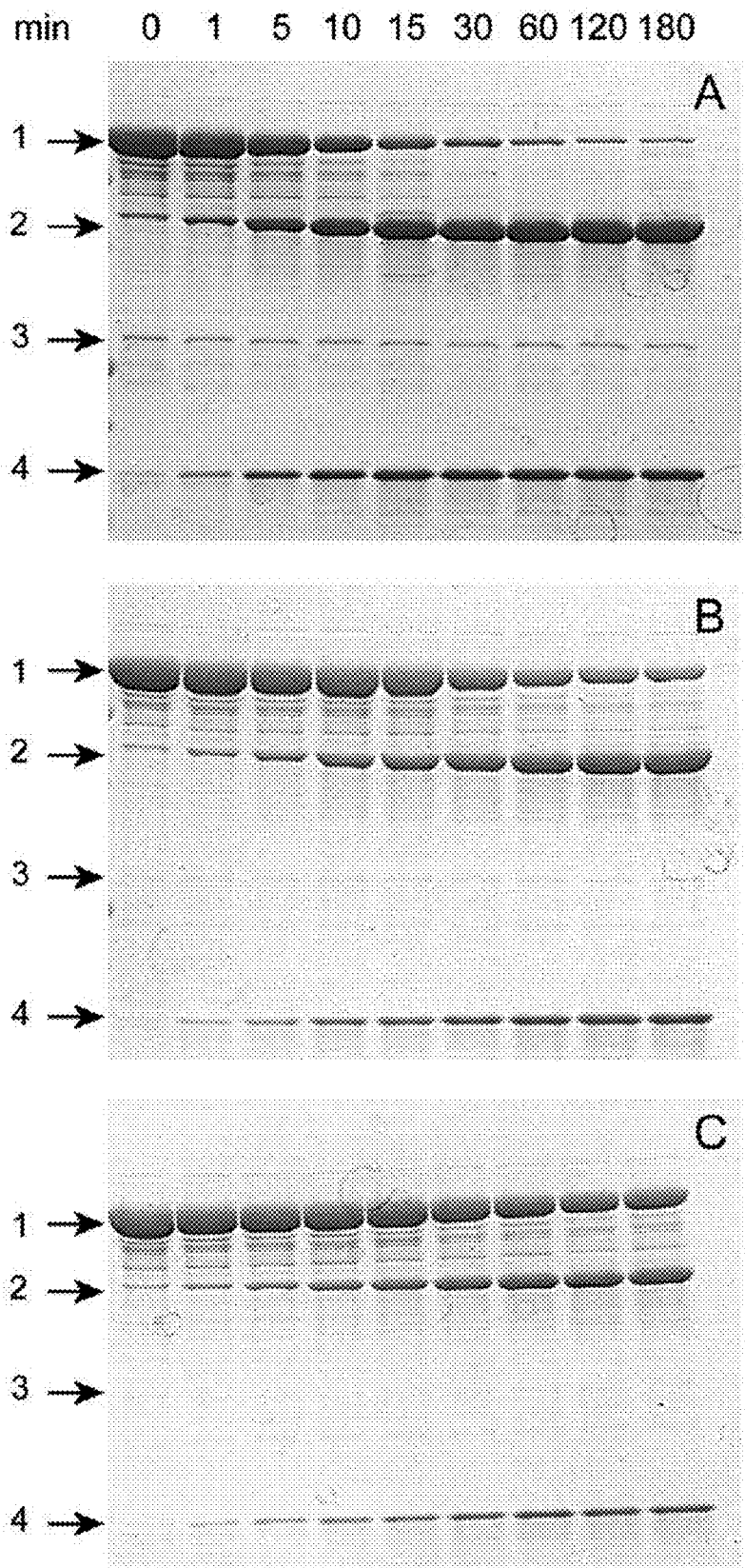
FIG. 6 (A-C) depicts images of Coomassie-stained denaturing gel electrophoresis (SDS-PAGE) showing the time and concentration dependence of proteolysis of His8-MBP-fl-cytb5 in the presence of TEV protease to release fl-cytb5.

Vectors pVP55A and pVP56K allow TEV protease-dependent cleavage of a fusion protein to release the target protein from either His8- or His8-MBP, respectively. FIG. 6 depicts an image of a Coomassie-stained SDS-PAGE gel showing the time and concentration dependence of proteolysis of His8-MBP-fl-cytb5 in the presence of TEV protease to release fl-cytb5. In FIG. 6(A) the TEV protease was present at ratio of 1:10 relative to His8-MBP-fl-cytb5. In FIG. 6(B) the TEV protease was present at ratio of 1:50 relative to His8-MBP-fl-cytb5. In FIG. 6(C) the TEV protease was present at ratio of 1:100 relative to His8-MBP-fl-cytb5. In all three panels, arrows (1) indicate His8-MBP-fl-cytb5, arrows (2) indicate His 8-MBP, arrows (3) indicate TEV protease, arrows (4) indicate fl-cytb5.

FIG. 6 shows that fl-cytb5 could be stoichiometrically released from His 8-MBP-fl-cytb5 by treatment with TEV protease. In these experiments, a satisfactory reaction was obtained at a ratio of His8-MBP-fl-cytb5 to TEV protease of 10:1 (reaction completed in 30 min). Lower amounts of TEV protease also catalyzed the proteolysis reaction, albeit with a longer, less practical amount of time required to reach completion.

Incorporation of cytb5 into Liposomes

The highly soluble and easily handled His8-MBP-fl-cytb5 can be used for the in situ delivery of fl-cytb5 to a membrane environment. FIG. 7A shows a schematic representation of this approach. For this experiment, the TEV protease reaction was performed in the presence of radiolabeled liposomes. The liposome fraction was then fractionated by density gradient ultracentrifugation. The liposomes and bound protein float owing to their low density. In contrast, proteins not associated with the liposomes will have a higher density and will thus be separated by the ultracentrifugation. Samples were taken from different points in the gradient and analyzed for lipid content by scintillation counting and for protein content by denaturing gel electrophoresis.

Figure 7:
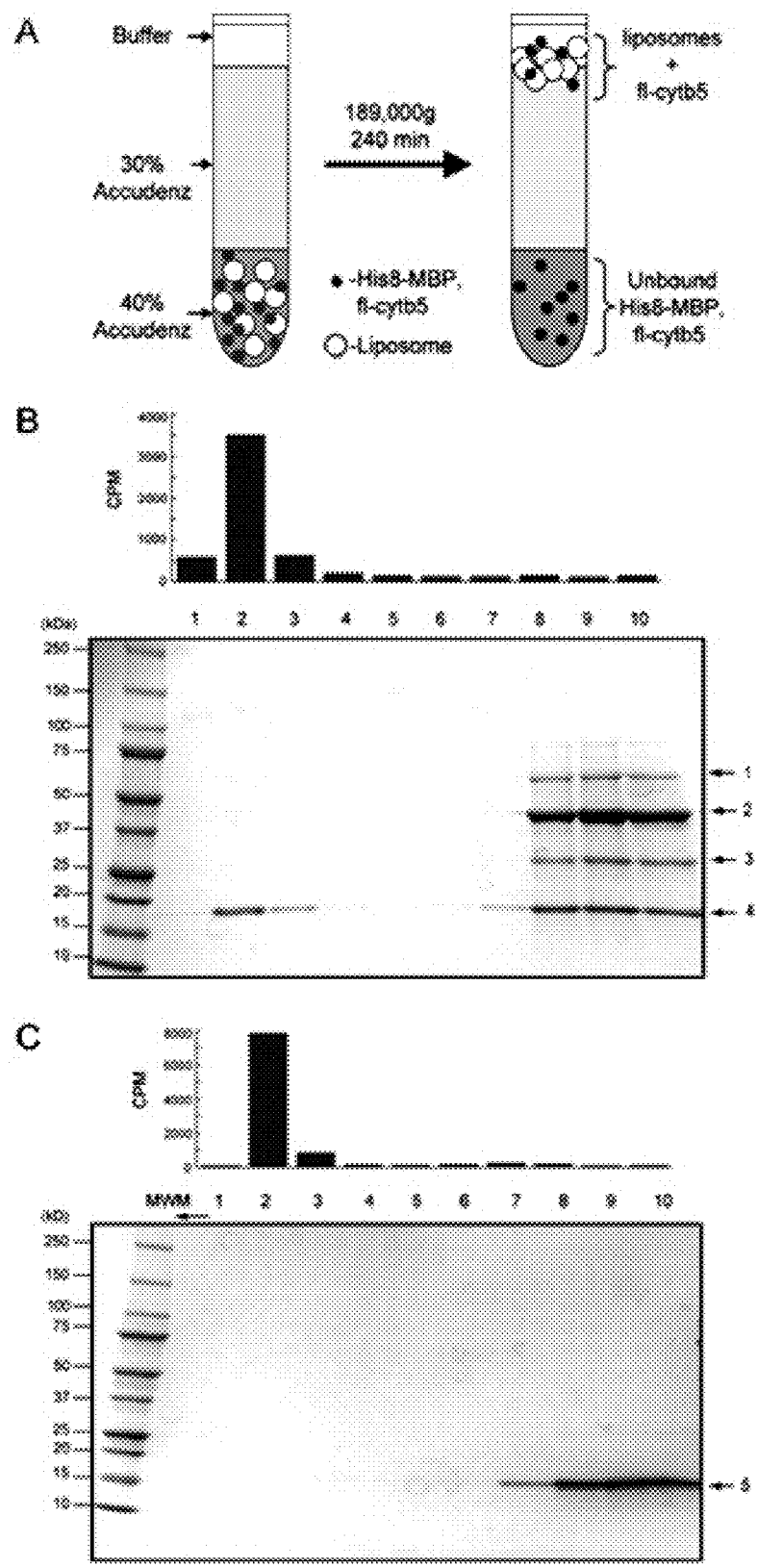
FIG. 7 depicts a diagram of the experiment (A) and graphs and images (B, C) of Coomassie-stained SDS-PAGE gels showing incorporation of fl-cytb5 into phospholipids vesicles.

FIG. 7 shows incorporation of fl-cytb5 into phospholipids vesicles. FIG. 7A: a schematic representation of the liposome floating experiment. The open circles represent the liposomes and the solid black circles represent proteins, including His8-MBP-fl-cytb5 and fl-cytb5 and TEV protease. Protein bound to the liposome will migrate to the interface between buffer and 30% Accudenz, while unbound proteins will remain in the 40% Accudenz layer. FIG. 7B: alignment of scintillation counting results (detects [$^3$H]-1,2-dipalmitoyl phosphatidylcholine added as a tracer to the liposome preparation) of the fractions collected from top to bottom from the liposome floating experiment with a Coomassie-stained denaturing gel. Lanes 1-3 contain the liposomes and fl-cytb5 (arrow 4). His8-MBP and TEV protease did not bind to liposomes. In control experiments, His8-MBP-fl-cytb5 was also bound to liposomes in the absence of TEV protease. Lanes 8-10 contain residual His8-MBP-fl-cytb5 (arrow 1), His8-MBP (arrow 2), TEV protease (arrow 3), and unbound fl-cytb5 (arrow 4). FIG. 7C: alignment of scintillation counting results ([$^3$H] lipid) with Coomassie-stained denaturing gel for exposure of cytb5-sd to liposomes. Cytb5-sd (arrow 5) did not bind to liposomes.

FIG. 7B shows the results of the liposome incorporation experiment performed with His8-MBP-fl-cytb5. The bar graph above the gel shows the position of $^3$H-labeled phosphatidylcholine detected in the samples taken from the ultracentrifugation gradient, while the denaturing electrophoresis gel shows the proteins present in the different fractions from the gradient. Near quantitative proteolysis of fl-cytb5 was obtained. Moreover, the lipid containing fractions contained a significant fraction (approximately 25-50%) of the total released fl-cyt5. His 8-MBP did not associate with the liposomes.

FIG. 7C shows a comparable liposome incorporation experiment performed with His8-cytb5-sd, which lacks the requisite membrane anchor. In this case, no incorporation of cytb5-sd into the vesicle fraction was observed.

Auto-induction

The powerful approach of auto-induction to high-throughput structural biology is based on bacterial diauxic growth in the presence of glucose and lactose. Some principles on the use of auto-induction with this vector platform are reported elsewhere (Blommel et al., 2007, *Biotechnol. Prog.* 23: 585-598). In previous work on the use of lactose as an inducer of bacterial protein expression, this approach was found to lead to high-level incorporation of iron into iron-containing proteins (Hoffman et al., 1995, *Protein Expr. Purif.* 6: 646-654). It was postulated that this favorable result arose from the slow onset of recombinant protein expression and continued cellular metabolism allowed by lactose-derived induction. This would contrast with the strong disruption of cellular growth and metabolism enforced by batch addition of IPTG.

When auto-induction was used to express the soluble forms of cytb5, whether as a domain alone or as a fusion to MBP, an increased amount of heme was revealed by the intense red color of the harvested cells. The assumption is that this would also correspond to an increased incorporation of heme into the expressed cytb5. Indeed, this appears to be true for cytb5-sd, which could be purified by Ni IMAC with a high-level of heme incorporation. In contrast, expression of the insoluble His8-fl-cytb5 or a short time induction of soluble His8-MBP-fl-cytb5 with IPTG did not stimulate heme incorporation.

These finding are both consistent with the concept that auto-induction allows a smooth transition of the expression host from an un-induced to induced state under control of natural metabolic processes (Hoffman et al., 1995, *Protein Expr. Purif.* 6: 646-654). In this case, the need for increased heme biosynthesis was apparently signaled by accumulation of a soluble heme binding protein, but not by expression of an insoluble variant. With soluble expression, the auto-induction process permitted the transcription and translation of the natural biosynthetic genes needed to increase heme content. This is remarkably different from the near instantaneous shutdown of many important cellular functions initiated by the batch addition of IPTG, and corresponding to a lowered prospect for obtaining heme incorporation.

Purification of fl-cytb5

Several procedures for the expression, solubilization, and incorporation of heme into fl-cytb5 expressed in *E. coli* have been developed. These require solubilization of the precipitated protein from bacterial membranes by addition of chaotropes and detergents, refolding of the solubilized proteins, heme incorporation, and further purification steps (Mulrooney and Waskell, 2000, *Protein Expr. Purif.* 19: 173-178; Nguyen et al., 2004, *J. Struct. Funct. Genomics* 5: 23-27).

The data presented here show how expression of His8-MBP-fl-cytb5 for a short time with IPTG induction gives rise to a fully soluble fusion protein that can be purified to homogeneity without the use of detergents and without the requirement for refolding the protein. When amylose affinity chromatography was used to purify His8-MBP-fl-cytb5 and possibly avoid loss of heme, this method gave a considerably less pure protein preparation after a single step with significant protein loss and furthermore did not address the low heme incorporation in fl-cytb5 obtained from IPTG induction. Due to these experimental deficiencies and also due to the higher cost of the amylose resin, Ni IMAC and in vitro heme reconstitution emerged as the best option for purification of the His8-MBP-fl-cytb5 obtained from IPTG induction.

His8-MBP-fl-cytb5 was found to be a suitable substrate for soluble cytb5R and the VIK values for the fusion protein and cytb5-sd alone differed by only approximately 3-fold (Table 5). The mechanism of electron transfer between cytb5 and cytb5R is not clearly understood, but recent reports suggest that the interaction and electron transfer between cytb5 and its partners occur via a dynamic docking mechanism in which a large ensemble of weakly bound protein-protein configurations contribute to binding, but only a few are productive in electron transfer. The minor differences in $V_{max}$ observed for His8-MBP-fl-cytb5 and cytb5-sd may represent differences in this docking process leading to the productive electron transfer complex.

In situ Delivery of Monotonic Membrane Proteins to Liposomes

Several elegant experiments have shown that fl-cytb5 spontaneously associates with cellular membranes (Yabal et al., 2003, *J. Biol. Chem.* 278: 3489-3496; Stefanovic et al., 2007, *Cell* 128: 1147-1159). This natural property was exploited in order to use His8-MBP-fl-cytb5 as a delivery vehicle for incorporation into biologically relevant membrane environments (in this case, a synthetic liposome). The results of FIG. 7 show that while fl-cytb5 liberated by proteolysis could be effectively transferred into the liposome, cytb5-sd lacking the membrane anchor could not. One skilled in the art may further optimize the ratio of liposome and time for membrane insertion in order to possibly obtain higher level of capture of the released fl-cytb5. In the examples described herein, this in situ delivery method proceeds directly in the presence of the desired liposome, and is not complicated by the presence of additional detergents. Bulk proteolysis in a rapid manner is also facilitated by the availability of gram quantities of highly active TEV protease obtained from an alternative use of this vector platform and auto-induction (Blommel and Fox, 2007, *Protein Expr. Purif.* 55: 53-68).

Other experiments showed that His8-MBP-fl-cytb5 would also associate with the liposome fraction in the absence of TEV protease. Therefore, the cytb5 membrane anchor might be used as a C-terminal fusion to facilitate spontaneous association of other proteins with a membrane fraction. In addition, proteolysis of His8-MBP-fl-cytb5 may occur either in solution or as the membrane-associated complex.

It is to be understood that this invention is not limited to the particular devices, methodology, protocols, subjects, or reagents described, and as such may vary. It is also to be understood that the terminology used herein is for the purpose of describing particular embodiments only, and is not intended to limit the scope of the present invention, which is limited only by the claims. Other suitable modifications and adaptations of a variety of conditions and parameters, obvious to those skilled in the art of genetic engineering, molecular biology, and biochemistry, are within the scope of this invention. All publications, patents, and patent applications cited herein are incorporated by reference in their entirety for all purposes.

What is claimed is:

1. A system for expressing a membrane polypeptide, the system comprising:
   a) a recombinant expression vector capable of expressing a fusion protein that comprises
      i. a solubilizing agent,
      ii. a functional membrane polypeptide comprising a membrane anchor that comprises an amino acid sequence
         1. at least 90% identical to the amino acid sequence of SEQ ID NO:7 or;
         2. an amino acid sequence of SEQ ID NO:7 having 1 to 4 conservative amino acid substitutions; and
      iii. a linker that is interposed between the solubilizing agent and the functional membrane polypeptide, wherein when the linker is intact, the functional membrane polypeptide is soluble; and
   b) a cleaver capable of cleaving the linker to release the functional membrane polypeptide, wherein, when the fusion protein is expressed, the linker can be cleaved by the cleaver to allow association of the functional membrane polypeptide with a membrane.

2. The system of claim 1 wherein the fusion protein is a soluble fusion protein.

3. The system of claim 1 wherein the solubilizing agent is a maltose binding protein.

4. The system of claim 1 wherein the membrane anchor comprises an amino acid sequence at least 90% identical to the amino acid sequence of SEQ ID NO:6, or an amino acid sequence of SEQ ID NO:6 having 1 to 2 conservative amino acid substitutions.

5. The system of claim 1 wherein the fusion protein further comprises an affinity purification tag.

6. The system of claim 1 wherein the membrane polypeptide is a cytochrome b5.

7. The system of claim 1 wherein the cleaver is a protease.

8. The system of claim 1 wherein the cleaver is a tobacco etch virus (TEV) protease, a human rhinovirus 3C protease, or a tobacco vein mottling virus (TVMV) protease.

9. The system of claim 1 wherein the fusion protein further comprises a protease capable of cleaving said linker.

10. The system of claim 1 wherein the linker is about 4 to about 60 amino acid residues long.

11. The system of claim 1 wherein the membrane comprises at least one of a lipid vesicle, a liposome, or a microsome.

12. A method for in vitro association of a membrane polypeptide with a membrane, said method comprises providing the expression system of claim 1 and cleaving the linker to release the membrane polypeptide, wherein, when the linker is cleaved, the membrane polypeptide associates with the membrane.

13. The method of claim 12 wherein the fusion protein is a soluble fusion protein.

14. The method of claim 12 wherein the solubilizing agent is a maltose binding protein.

15. The method of claim 12 wherein the membrane anchor comprises an amino acid sequence at least 90% identical to the amino acid sequence of SEQ ID NO:6, or an amino acid sequence of SEQ ID NO:6 having 1 to 2 conservative amino acid substitutions.

16. The method of claim 12 wherein the fusion protein further comprises an affinity purification tag.

17. The method of claim 12 wherein the membrane protein is a cytochrome b5.

18. The method of claim 12 wherein the cleaver is a protease.

19. The method of claim 12 wherein the cleaver is a tobacco etch virus (TEV) protease, a human rhinovirus 3C protease, or a tobacco vein mottling virus (TVMV) protease.

20. The method of claim 12 wherein the fusion protein further comprises a protease capable of cleaving said linker.

21. The method of claim 12 wherein the membrane comprises at least one of a lipid vesicle, a liposome, or a microsome.

22. The method of claim 12 wherein the expression of the fusion protein and the cleaving of the linker are temporally separated from each other.

* * * * *

```
                            SEQUENCE LISTING

<160> NUMBER OF SEQ ID NOS: 9

<210> SEQ ID NO 1
<211> LENGTH: 34
<212> TYPE: DNA
<213> ORGANISM: Artificial
<220> FEATURE:
<223> OTHER INFORMATION: fl-cytb5 forward primer

<400> SEQUENCE: 1
ttcggcgatc gccgaaatgg cagaacaaag cgac                             34

<210> SEQ ID NO 2
<211> LENGTH: 36
<212> TYPE: DNA
<213> ORGANISM: Artificial
<220> FEATURE:
<223> OTHER INFORMATION: fl-cytb5 reverse primer

<400> SEQUENCE: 2
agcagtttaa acttagtcct ctgccatgta taggcg                           36

<210> SEQ ID NO 3
<211> LENGTH: 36
<212> TYPE: DNA
<213> ORGANISM: Artificial
<220> FEATURE:
<223> OTHER INFORMATION: cytb5-sd reverse primer

<400> SEQUENCE: 3
agcagtttaa acttacggtt ccggcggttt gttcag                           36

<210> SEQ ID NO 4
<211> LENGTH: 37
<212> TYPE: DNA
<213> ORGANISM: Artificial
<220> FEATURE:
<223> OTHER INFORMATION: human cytochrome b5 reductase forward primer

<400> SEQUENCE: 4
ttcggcgatc gccatgaagc tgttccagcg ctccacg                          37

<210> SEQ ID NO 5
<211> LENGTH: 33
<212> TYPE: DNA
<213> ORGANISM: Artificial
<220> FEATURE:
<223> OTHER INFORMATION: human cytochrome b5 reductase reverse primer

<400> SEQUENCE: 5
tcgtgtttaa actcagaaga cgaagcagcg ctc                              33

<210> SEQ ID NO 6
<211> LENGTH: 19
<212> TYPE: PRT
<213> ORGANISM: Homo sapiens

<400> SEQUENCE: 6
```

Pro Ala Ile Ser Ala Val Ala Val Ala Leu Met Tyr Arg Leu Tyr Met
1               5                   10                  15

Ala Glu Asp

<210> SEQ ID NO 7
<211> LENGTH: 37
<212> TYPE: PRT
<213> ORGANISM: Homo sapiens

<400> SEQUENCE: 7

Thr Leu Ile Thr Thr Ile Asp Ser Ser Ser Trp Trp Thr Asn Trp
1               5                   10                  15

Val Ile Pro Ala Ile Ser Ala Val Ala Val Ala Leu Met Tyr Arg Leu
            20                  25                  30

Tyr Met Ala Glu Asp
        35

<210> SEQ ID NO 8
<211> LENGTH: 538
<212> TYPE: PRT
<213> ORGANISM: Homo sapiens

<400> SEQUENCE: 8

Met Gly His His His His His His Ala Ser Lys Ile Glu Glu
1               5                   10                  15

Gly Lys Leu Val Ile Trp Ile Asn Gly Asp Lys Gly Tyr Asn Gly Leu
            20                  25                  30

Ala Glu Val Gly Lys Lys Phe Glu Lys Asp Thr Gly Ile Lys Val Thr
            35                  40                  45

Val Glu His Pro Asp Lys Leu Glu Glu Lys Phe Pro Gln Val Ala Ala
        50                  55                  60

Thr Gly Asp Gly Pro Asp Ile Ile Phe Trp Ala His Asp Arg Phe Gly
65                  70                  75                  80

Gly Tyr Ala Gln Ser Gly Leu Leu Ala Glu Ile Thr Pro Asp Lys Ala
                85                  90                  95

Phe Gln Asp Lys Leu Tyr Pro Phe Thr Trp Asp Ala Val Arg Tyr Asn
            100                 105                 110

Gly Lys Leu Ile Ala Tyr Pro Ile Ala Val Glu Ala Leu Ser Leu Ile
            115                 120                 125

Tyr Asn Lys Asp Leu Leu Pro Asn Pro Pro Lys Thr Trp Glu Glu Ile
        130                 135                 140

Pro Ala Leu Asp Lys Glu Leu Lys Ala Lys Gly Lys Ser Ala Leu Met
145                 150                 155                 160

Phe Asn Leu Gln Glu Pro Tyr Phe Thr Trp Pro Leu Ile Ala Ala Asp
                165                 170                 175

Gly Gly Tyr Ala Phe Lys Tyr Glu Asn Gly Lys Tyr Asp Ile Lys Asp
            180                 185                 190

Val Gly Val Asp Asn Ala Gly Ala Lys Ala Gly Leu Thr Phe Leu Val
            195                 200                 205

Asp Leu Ile Lys Asn Lys His Met Asn Ala Asp Thr Asp Tyr Ser Ile
        210                 215                 220

Ala Glu Ala Ala Phe Asn Lys Gly Glu Thr Ala Met Thr Ile Asn Gly
225                 230                 235                 240

Pro Trp Ala Trp Ser Asn Ile Asp Thr Ser Lys Val Asn Tyr Gly Val
                245                 250                 255

Thr Val Leu Pro Thr Phe Lys Gly Gln Pro Ser Lys Pro Phe Val Gly

```
              260             265             270
Val Leu Ser Ala Gly Ile Asn Ala Ala Ser Pro Asn Lys Glu Leu Ala
            275             280             285

Lys Glu Phe Leu Glu Asn Tyr Leu Leu Thr Asp Glu Gly Leu Glu Ala
        290             295             300

Val Asn Lys Asp Lys Pro Leu Gly Ala Val Ala Leu Lys Ser Tyr Glu
305             310             315             320

Glu Glu Leu Ala Lys Asp Pro Arg Ile Ala Ala Thr Met Glu Asn Ala
            325             330             335

Gln Lys Gly Glu Ile Met Pro Asn Ile Pro Gln Met Ser Ala Phe Trp
            340             345             350

Tyr Ala Val Arg Thr Ala Val Ile Asn Ala Ala Ser Gly Arg Gln Thr
            355             360             365

Val Asp Glu Ala Leu Lys Asp Ala Gln Thr Leu Ile Asn Gly Asp Gly
        370             375             380

Ala Gly Leu Glu Val Leu Phe Gln Gly Pro Glu Asn Leu Tyr Phe Gln
385             390             395             400

Ala Ile Ala Glu Met Ala Glu Gln Ser Asp Glu Ala Val Lys Tyr Tyr
                405             410             415

Thr Leu Glu Glu Ile Gln Lys His Asn His Ser Lys Ser Thr Trp Leu
            420             425             430

Ile Leu His His Lys Val Tyr Asp Leu Thr Lys Phe Leu Glu Glu His
            435             440             445

Pro Gly Gly Glu Glu Val Leu Arg Glu Gln Ala Gly Gly Asp Ala Thr
        450             455             460

Glu Asn Phe Glu Asp Val Gly His Ser Thr Asp Ala Arg Glu Met Ser
465             470             475             480

Lys Thr Phe Ile Ile Gly Glu Leu His Pro Asp Asp Arg Pro Lys Leu
                485             490             495

Asn Lys Pro Pro Glu Thr Leu Ile Thr Ile Ile Asp Ser Ser Ser Ser
            500             505             510

Trp Trp Thr Asn Trp Val Ile Pro Ala Ile Ser Ala Val Ala Val Ala
            515             520             525

Leu Met Tyr Arg Leu Tyr Met Ala Glu Asp
        530             535

<210> SEQ ID NO 9
<211> LENGTH: 19
<212> TYPE: PRT
<213> ORGANISM: Homo sapiens

<400> SEQUENCE: 9

Pro Ala Ile Ser Ala Val Ala Val Ala Leu Met Tyr Arg Leu Tyr Met
1               5                   10                  15

Ala Glu Asp
```